US007456954B2

(12) United States Patent
Weiss et al.

(10) Patent No.: US 7,456,954 B2
(45) Date of Patent: Nov. 25, 2008

(54) MODULATED EXCITATION FLUORESCENCE ANALYSIS

(75) Inventors: Shimon Weiss, Los Angeles, CA (US); Achillefs Kapanidis, Oakland, CA (US); Ted A. Laurence, Livermore, CA (US); Nam K. Lee, Seoul (KR)

(73) Assignee: The Regents of the University of California, Oakland, CA (US)

( * ) Notice: Subject to any disclaimer, the term of this patent is extended or adjusted under 35 U.S.C. 154(b) by 192 days.

(21) Appl. No.: 10/561,448

(22) PCT Filed: Jun. 17, 2004

(86) PCT No.: PCT/US2004/019709

§ 371 (c)(1), (2), (4) Date: Dec. 20, 2005

(87) PCT Pub. No.: WO2005/008212

PCT Pub. Date: Jan. 27, 2005

(65) Prior Publication Data

US 2007/0109536 A1 May 17, 2007

Related U.S. Application Data

(60) Provisional application No. 60/572,559, filed on May 18, 2004, provisional application No. 60/480,346, filed on Jun. 20, 2003.

(51) Int. Cl.
*G01J 3/30* (2006.01)
*G01N 21/64* (2006.01)

(52) U.S. Cl. .................... 356/318; 356/417; 250/458.1; 436/172

(58) Field of Classification Search ................. 356/317, 356/318, 417; 250/458.1, 459.1, 461.1, 461.2; 436/172

See application file for complete search history.

(56) References Cited

U.S. PATENT DOCUMENTS

| | | | |
|---|---|---|---|
| 4,162,851 | A | 7/1979 | Wada |
| 5,149,972 | A | 9/1992 | Fay et al. |

(Continued)

FOREIGN PATENT DOCUMENTS

| | | | |
|---|---|---|---|
| DE | 102 10 737 | A1 | 3/2003 |

OTHER PUBLICATIONS

Adams, S.R., et al., New Biarsenical Ligands and Tetracysteine Motifs for Protein Labeling in Vitro and in Vivo: Synthesis and Biological Applications. J. Am. Chem. Soc., 2002. 124(21): p. 6063-6076.

(Continued)

*Primary Examiner*—F. L Evans
(74) *Attorney, Agent, or Firm*—Venable, LLP; Henry J. Daley

(57) ABSTRACT

Fluorescence, spectroscopy is used to analyze small numbers of molecules that are present in a relatively small detection volume or zone. Information regarding physical and chemical properties of these molecules is determined by rapidly modulating the wavelength, intensity and/or polarization of laser energy to excite fluorophores that are attached either to the molecule of interest or a molecule that interacts with the molecule of interest. The emission profile of the fluorophores is used to determine useful information about the labeled and/or non-labeled molecules including molecular interactions between the molecules.

38 Claims, 16 Drawing Sheets

U.S. PATENT DOCUMENTS

| | | | | |
|---|---|---|---|---|
| 5,233,197 | A | 8/1993 | Bowman et al. | |
| 5,784,157 | A | 7/1998 | Gorfinkel et al. | |
| 5,807,677 | A | 9/1998 | Eigen et al. | |
| 5,933,233 | A | 8/1999 | Gunther | |
| 6,122,098 | A | 9/2000 | Kask et al. | |
| 6,137,584 | A | 10/2000 | Seidel | |
| 6,140,048 | A | 10/2000 | Muller et al. | |
| 6,200,818 | B1 | 3/2001 | Eigen et al. | |
| 6,208,815 | B1 | 3/2001 | Seidel et al. | |
| 6,376,843 | B1 | 4/2002 | Palo | |
| 6,407,856 | B1 | 6/2002 | Kask et al. | |
| 6,444,476 | B1 | 9/2002 | Morgan | |
| 6,498,017 | B2 | 12/2002 | Riesner et al. | |
| 6,515,289 | B1 | 2/2003 | Kask | |
| 6,556,296 | B1 | 4/2003 | Palo | |
| 7,223,985 | B2 * | 5/2007 | Rigler et al. | 250/458.1 |
| 2003/0059811 | A1 | 3/2003 | Djaballah et al. | |

OTHER PUBLICATIONS

Beliaev, A.S., et al., Gene and Protein Expression Proftles of *Shewanella oneidensis* during Anaerobic Growth with Dfferent Electron Acceptors. OMICS, 2002. 6(1): p. 39-60.
Bewley, C.A., A.M. Gronenborn, and G.M. Clore, Minor Groove-Binding Architectural Proteins: Structure, Function, and DNA Recognition. Annual Review of Biophysics and Biomolecular Structure, 1998. 27(1): p. 105-131.
Bruchez, M., Jr., Moronne, M., Gin, P., Weiss, S. and Alivisatos, A.P. (1998) Science 281, 2013-6.
Chen, Y., Müller, J.D., So, P.T. and Gratton, E. (1999) Biophysical Journal 77, 553-67.
Chen, Y., Müller, J.D., Tetin, S.Y., Tyner, J.D. and Gratton, E. (2000) Biophysical Journal 79, 1074-1084.
Clegg, R.M. (1992) Methods Enzymol 211, 353-88.
Dahan, M., Deniz, A.A. Ha, T., Chemla, D.S., Schultz, P.G. and Weiss, S. (1999) Chemical Physics 247, 85-106.
Delneri, D., Brancia, F.L. and Oliver, S.G. (2001) Curr Opin Biotechnol 12, 87-91.
Deniz, A.A. et al. (2000) Proc Natl Acad Sci U S A 97, 5179-84.
Deniz, A.A., Dahan, M., Grunwell, J.R, Ha, T., Faulhaber, A.E., Chemla, D.S., Weiss, S. and Schultz, P.G. (1999) Proceedings of the National Academy of Sciences of the United States of America 96, 3670-5.
Eggeling, C., Fries, J.R., Brand, L., Günther, R and Seidel, C.A. (1998) Proceedings of the National Academy of Sciences of the United States of America 95, 1556-61.
Eggeling, C., Widengren, J., Rigler, R and Seidel, C.A.M. (1998) Anal chem 70, 2651-2659.
Feldhaus, M., et al., Flow-cytometric isolation of human antibodies from a nonimmune *Saccharomyces cerevisiae* surface display library. Nat Biotechnol., 2003. 21(2): p. 163-70.
Fries, J.R, Brand, L., Eggeling, C., Kollner, M. and Seidel, C.A.M. (1998) Journal of Physical Chemistry a 102, 6601-6613.
Giometti CS, K.T., Tollaksen SL, Tsapin A, Zhu W, Yates JR 3rd, Nealson KH., Analysis of the *Shewanella oneidensis* proteome by two-dimensional gel electrophoresis under nondenaturing conditions. Proteomics, 2003. 3(5): p. 777-85.
Ha, T., Enderle, T., Ogletree, D.F., Chemla, D.S., Selvin, P.R. and Weiss, S. (1996) Proc Natl Acad Sci U S A 93, 6264-8.
Ha, T., Rasnik, I., Cheng, W., Babcock, H.P., Gauss, G.H., Lohman, T.M. and Chu, S. (2002) Nature 419, 638-41.
Ha, T., Ting, A.Y., Liang, J., Caldwell, W.B., Deniz, A.A., Chemla, D.S., Schultz, P.G. and Weiss, S. (1999) Proc Natl Acad Sci U S A 96, 893-8.
Ha, T., Zhuang, X., Kim, H., Orr, J., Williamson, J. and Chu, S. (1999) Proc Natl Acad Sci U S A 96, 9077-9082.
Hazbun, T.R. and Fields, S. (2001) Proc Natl Acad Sci U S A 98, 4277-8.
Heinze, K.G., Koltermann, A. and Schwille, P. (2000) Proceedings of the National Academy of Sciences of the United States of America 97, 10377-82.
Heyduk, E., Fei, Y. and Heyduk, T. (2003) Comb Chem High Throughput Screen 6, 347-54.
Heyduk, E., Knoll, E. and Heyduk, T. (2003) Anal Biochem 316, 1-10.
Heyduk, T. and Heyduk, E. (2002) Nat Biotechnol 20, 171-6.
Hoch, J.A. and T.J. Silhavy, eds. Two-Component Signal Transduction. 1995, ASM Press: Washington, D.C.
Holden, JA. (2001) Curr Mod Chem Anti-Canc Agents 1, 1-25.
Ito, T., Chiba, T., Ozawa, R., Yoshida, M., Hattori, M. and Sakaki, Y. (2001) Proc Nall Acad Sci U S A 98, 4569-74.
Kapanadis, A., et al. Single-Molecule Analysis of Sigma Factor Release. Annual Biophysical Society Meeting, San Antonio, 2003.
Kapanadis, A.N., et al. Fluorescence-aided molecule sorting: Analysis of structure and interactions by alternating-laser excitation of single molecules. PNAS 2004, 101:24 8936-8941.
Kapanidis, A.N., and S. Weiss, Fluorescent probes and bioconjugation chemistries for single-molecule fluorescence analysis of biomolecules. Journal of Chemical Physics, 2002. 117(24): p. 10953-10964.
Kapanidis, A.N., Ebright, Y.W. and Ebright, R.H. (2001) J Am Chem Soc 123, 12123-5.
Kask, P. et al. (2000) Biophys J 78, 1703-13.
Kask, P., Palo, K., Ullmann, D. and Gall, K. (1999) Proc Natl Acad Sci U S A 96, 13756-61.
Kettman JR, F.J., Lefkovits L, Proteome, transciptonte and genome: top down or bottom up analysis? Biomol Eng., 2001. 18(5): p. 207-12.
Kinjo, M. and Rigler, R (1995) Nucleic Acids Res 23, 1795-9.
Ko, D.S., Sauer, M., Nord, S., Müller, R. and Wolfrum, J. (1997) Chemical Physics 269, 54-58.
Kohl, T., Heinze, K.G., Kuhlemann, R., Koltermann, A. and Schwille, P. (2002) Proc Natl Acad Sci U S A 99, 12161-6.
Kolasa IK, L.T., Wierzchowski KL., Effect of A(n) tracts within the UP element proximal subsite of a model promoter on kinetics of open. complex formation by *Escherichia coli* RNA polymerase. Acta Biochim Pol., 2002. 49(3): p. 659-69.
Lacoste, T.D., Michalet, X., Pinaud, F., Chemla, D.S., Alivisatos, A.P. and Weiss, S. (2000) Proc Natl Acad Sci U S A 97, 9461-6.
Laurence, T.A. and S. Weiss, Analytical Chemistry: How to Detect Weak Pairs. Science, 2003. 299(5607): p. 667-668.
Lee, J., et al., Phosphorylation-Induced Signal Propagation in the Response Regulator NtrC J. Bacteriol., 2000. 182(18): p. 5188-5195.
Lee, L.G. et al. (1997) Nucleic Acids Res 25, 2816-22.
Legrain, P. and Selig, L. (2000) FEBS Left 480, 32-6.
Levene, M.J,. Korlach, J., Turner, S.W., Foquet, M., Craighead, H.G. and Webb, W.W. (2003) Science 299, 682-6.
Liu, J. and Lu, Y. (2002) J. Am. Chem. Soc. 124, 15208-16.
Lorenz, M., et al., Global structure similarities of intact and nicked DNA complexed with IHF measured in solution by fluorescence resonance energy transfer. Nucl. Acis. Res., 1999. 27(23): p. 4619-4625.
Magde, D., Elson, E. and Webb, W.W. (1972) Physical Review Letters 29, 705-8.
Mendelsohn, A.R. and Brent, R (1999) Science 284, 1948-50.
Nooren, I.M.A. and J.M. Thornton, New EMBO Member's Review: Diversity of protein protein interactions. EMBO J., 2003. 22(14): p. 3486-3492.
Oliver, S. (2000) Nature 403, 601-3.
Palo, K., Mets, U., Jäger, S., Kask, P. and Gall, K. (2000) Biophysical Journal 79, 2858-66.
Pandolfi, P.P. (2001) Oncogene 20, 3116-27.
Porter SC, N.A., Wedel AB, Kustu S., Oligomerization of NTRC at the glnA Enhancer is required for transcriptional activation. Genes Dev., 1993. 7(11): p. 2258-73.
Qian, H. and Elson, E.L. (1990) Biophysical Journal 57,375-80.
Rauer, B., Neumann, E., Widengren, J. and Rigler, R. (1996) Biophys Chem 58,3-12.
Rippe, K., et al., Transcriptional Activation via DNA-looping: Visualization of Intermediates in the Activation Pathway of *E. coli* RNA Polymerase. [sigma] 54Holoenzyme by Scanning Force Microscopy. Journal of Molecular Biology, 1997. 270(2): p. 125-138.

Rippe, K., N. Mucke, and A. Schulz, Association States of the Transcription Activator Protein NtrC from *E. coli* Determined by Analytical Ultracentrifugation. Journal of Molecular Biology, 1998. 278(5): p. 915-933.
Rippe, K., Simultaneous Binding of Two DNA Duplexes to the NtrC-Enhancer Complex Studied by Two-Color Cross-Correlation Spectroscopy. Biochemistry, 2000. 39(9): p. 2131-2139.
Rombel, I, et al., MgATP Binding and Hydrolysis Determinants of NtrC, a Bacteriol Enhancer-Binding Protein. J. Bacteriol., 1999. 181(15): p. 4628-4638.
Rothwell, P.J. et al. (2003) Proc Natl Acad Sci U S A 100, 1655-60.
Santero E, H.T., North AK, Berger DK, Porter SC, Kustu S., Role of integration host factor in stimulating transcription from the sigma 54-dependent nifH promoter. J Mol Biol., 1992. 227(3): p. 602-20.
Schuler, B. and L.K. Pannell, Specific Labeling of Polypeptides at Amino-Terminal Cysteine Residues Using Cy5-benzyl Thioester. Bioconjugate Chem., 2002. 13(5); p. 1039-1043.
Schuler, B., Lipman, E.A. and Eaton, W.A. (2002) Nature 419, 743-7.
Schulz, A., et al., Scanning Force Microscopy of *Escherichia coli* RNA Polymerase. [sigma] 54Holoenzynme Complexes with DNA in Buffer and in Air,. Journal of Molecular Biology, 1998. 283(4): p. 821-836.
Schwille, P., Meyer-Almes, F.J. and Rigler, R (1997) Biophysical Journal 72, 1878-86.
Schwille, P., Oehlenschlager, F. and Walter, N.G. (1996) Biochemistry 35, 10182-93.
Selvin, P.R. (2000) Nat Struct Biol 7, 730-4.
Sevenich, F., et al., DNA binding and oligomerization of NtrC studied by fluorescence anisotropy and fluorescence correlation spectroscopy. Nucl. Acids. Res., 1998. 26(6): p. 1373-1381.
Su, W., et al., DNA-Looping and Enhancer Activity: Association Between DNA-Bound NtrC Activator and RNA Polymerase at the Bacterial glnA Promoter. PNAS, 1990. 87(14): p. 5504-5508.
Tintut, Y., J.T. Wang, and J.D. Gralla, Abortive Cycling and the Release of Polymerase for Elongation at the [MAGE] 54-dependent glnAp2 Promoter. J. Biol. Chem., 1995. 270(41): p. 24392-27398.
Uetz, P. (2002) Curr Opin Chem Biol 6, 57-62.
Uetz, P. et al. (2000) Nature 403, 623-7.
Wagner, R., Transcription Regulation in Prokaryotes. 2000, Oxford: Oxford University Press.
Wang, J.T. and J.D. Gralla, The Transcription Initiation Pathway of Sigma 54Mutants That Bypass the Enhancer Protein Requirement. Implications for the Mechanism of Activation. J. Biol. Chem., 1996. 271(51): p. 32707-32713.
Wyman, C., et al., Unusual Oligomerization Required for Activity of NtrC, a Bacterial Enhancer-Binding Protein. Science, 1997. 275(5306): p. 1658-1661.
Zhuang, X., Bartley, L.E., Babcock, H.P., Russell, R., Ha, T., Herschlag, D. and Chu, S. (2000) Science 288, 2048-51.
Zhuang, X., Kim, H., Pereira, M.J., Babcock, H.P., Walter, N.G. and Chu, S. (2002) Science 296, 1473-6.

* cited by examiner

S) NORMALIZED SUBPOPULATION CONCENTRATIONS $Y_D + Y_{DA} + Y_{DA} = 1$ $$Gg(0) = \frac{1}{N_{TOTAL}} \cdot \frac{Y_D + Y_{DA}(1-E)^2}{[Y_D + Y_{DA}(1-E)^2]}$$

$$Gr(0) = \frac{1}{N_{TOTAL}} \cdot \frac{Y_{DA}E^2k^2 + Y_A}{(Y_{DA}Ek + Y_A)^2}$$

$$Ggr(0) = \frac{1}{N_{TOTAL}} \cdot \frac{Y_{DA}(1-E)Ek}{[Y_D + Y_{DA}(1-E)][Y_{DA} + Ek + Y_A]}$$

MODULATED EXCITATION FLUORESCENCE ANALYSIS

CROSS-REFERENCE TO RELATED APPLICATION

This application claims priority to International Application No. PCT/US2004/019709, filed Jun. 17, 2004 and U.S. Provisional Application Nos. 60/572,559, filed May 18, 2004 and 60/480,346 filed Jun. 20, 2003, the entire contents of which are incorporated herein by reference.

This invention was made with support of Government Grant No. DE-FG03-02ER63339, awarded by DOE. The U.S. Government has certain rights in this invention.

BACKGROUND OF THE INVENTION

1. Field of the Invention

The present invention relates generally to analytical methods where fluorescence spectroscopy is used to analyze small numbers of molecules that are present in a relatively small detection volume or zone. More particularly, the present invention involves determining a wide variety of physical and chemical properties of one or more molecules by rapidly modulating the wavelength, intensity and/or polarization of beams of laser energy to excite fluorophores that are attached either to the molecule of interest or a molecule that interacts with the molecule of interest. The emission profile of the fluorophore is used to determine useful information about various properties of the labeled and/or non-labeled molecules including molecular interactions between the molecules 2. Description of Related Art The publications and other reference materials referred to herein to describe the background of the invention and to provide additional detail regarding its practice are hereby incorporated by reference. For convenience, the reference materials are numerically referenced and grouped in the appended bibliography. The contents of these publications and other reference materials are hereby incorporated by reference.

Understanding the intricate network of interactions occurring in cells allows probing of the mechanisms that control cell growth, maintenance and disease/death. Such interactions include protein-protein, protein-DNA, nucleic acid-nucleic acid, antibody-antigen, receptor-ligand, protein-drug and aggregation-inducing protein-protein interactions. Rapid, reliable and inexpensive methods that can characterize the multitude of the existing interactions is a core technology for proteomics, the scientific domain associated with the mapping of the complement of pair-wise protein-protein interactions on an organism-wide basis. Such interaction maps are necessary for the deciphering of the cell circuitry. Proteomic technologies are a prerequisite for interpreting, utilizing and leveraging the plethora of the genomic information available in the public domain. In-vitro and in-vivo screening of compound libraries against specific protein interactions will allow discovery of specific and powerful pharmaceuticals. Moreover, affordable versions of ultra-sensitive detection methods will an extremely useful tool for point-of-care diagnostics of a modem medical environment.

Several methods exist for evaluation of protein-protein interactions [1]. The yeast two-hybrid (Y2H) system, a genetic system based on the transcriptional activation of specific yeast genes [2-8] is a popular one. However, Y2H systems have limitations including complications associated with using protein fusions, incorrect protein folding, incorrect post-translational modification, potential toxicity of the proteins of interest in yeast, erratic reproducibility with large fraction of false positives and false negatives [1,3]. Additionally, since the observable of Y2H is based on DNA transcription, the Y2H method is not suited for the study of DNA transcription factors or DNA-binding proteins. Finally, use of Y2H requires several hours (due to the requirement of growing yeast cells) and cannot provide the accurate and complete characterization available for a homogeneous, solution-based, equilibrium-binding assay.

Development of optical methods that detect interactions in minute solution volumes and high-throughput screening (HTS) formats are highly desirable, since they represent rapid, inexpensive, reliable and non-invasive ways to determine binding constants, specificities, and half-lifetimes of the complexes of interacting partners.

Fluorescence detection with ultrahigh-sensitivity has led to the development of solution-based methods that study biomolecules and their interactions in small volumes (attoliter-femtoliter) and at low analyte concentrations (pM-nM). The first such method is fluorescence correlation spectroscopy (FCS), introduced to measure chemical kinetics and molecular diffusion by analysis of concentration fluctuations of a small ensemble of molecules [9]. FCS belong in a broader family of methods, often described as fluorescence-fluctuation spectroscopy (FFS). At very low concentrations, the fluctuations are manifested by well-resolved bursts of fluorescence corresponding to molecules traversing the confocal spot. These bursts are amenable to histogram-based methods. At higher concentrations, bursts are no longer resolved and the fluctuations are better analyzed by correlation-based methods.

Single-channel FCS (referring to a single emission channel) measures the autocorrelation of fluorescence fluctuations detected from an open detection volume including microfluidic flow systems and encapsulated molecules in small volumes, subjected to flow (or drift) and diffusion. The decay curve of the autocorrelation is used to identify changes in the diffusion time of a single species or changes in the relative contribution of subpopulations with different diffusion times. Single-channel FCS has been used to measure the kinetics of nucleic-acid hybridization [10,11] and of acetylcholine-receptor interaction [12]. However, since diffusion times scale proportionally with $m^{1/3}$ (m is mass), doubling the mass (e.g. due to protein homodimerization) increases the diffusion time only by 20%, a change difficult to measure with single-channel FCS and to use reliably for separating subpopulations.

Oligomerization of labeled monomeric biomolecules is also detectable by the increased brightness of the oligomers (compared to the monomer). For example, the tetramer $A_4$ is approximately 4 times brighter than the monomer A (excluding potential quenching of fluorophores). As a result, brightness-based analysis of interactions is more sensitive and robust than diffusion-time-based analysis. This property was exploited by methods that measure oligomerization using higher-order correlation and moment analysis of photon-count histograms [13]. Direct fitting of photon-count histograms with fixed time-bin width for determination of molecular brightness was introduced by Fluorescence Intensity Distribution Analysis (FIDA; [14]) and by Photon-Counting Histograms (PCH; [15]). These methods were used to analyze ligand-protein binding [16] and cleavage of hybridized DNA by restriction enzymes [14]. However, FIDA and PCH do not account for different diffusion times of different species. As a result, their extracted parameters are often skewed. Moreover, FIDA/PCH time bins are chosen to be much smaller than diffusion time (to assume that molecules are immobile during the chosen time bin), leading to complete loss of diffusion-time information for all species.

FIDA was extended to account for diffusion by plotting photon-count histograms for different time-bin widths simultaneously (Fluorescence Intensity Multiple Distribution Analysis, FIMDA [17]). Diffusion effects change the shape of the photon-count histogram, allowing global fitting of the histograms for all time-bin widths. This fitting extracts diffusion times, as well as brightness and concentration. However, FIMDA discards useful temporal information, such as the correlation between photons within a given time bin, as well as the correlation between successive time bins.

It is relatively difficult to distinguish between subpopulations in solution based on the observables available with single detection channel methods. Consider a simple equilibrium binding between two species A and B:

$$A+B \leftrightarrows AB$$

If one species is labeled with a fluorophore ($A^F$), then the species $A^F$ and $A^FB$ are distinguishable only by change in diffusion time across the detection volume. Species B must be much larger than species A for the difference to be detectable. If both A and B are labeled, then the species $A^FB^F$ is easier to separate, although it remains difficult since the change results in only a 2-fold change in fluorescence. Dual-channel methods provide greater resolving power than single-channel methods. Additionally, any Forster resonance energy transfer (FRET) occurring between the fluorophores on the two species $A^F$ and $B^F$ results in quenching, which results in a complex $A^FB^F$ which has two fluorophores, but not twice the brightness. With two different fluorophores detected in two detection channels, this drawback becomes an advantage, as discussed below.

To study interactions between two macromolecules using dual-channel methods, each is labeled with a fluorophore with a distinct emission wavelength rang. The fluorophores can be excited by a single- or dual-laser excitation source. If a protein A is labeled with a green-emitting fluorophore G (protein $A^G$), and a protein B is labeled with a red-emitting fluorophore R (protein $B^R$), association of the two proteins will yield $A^GB^R$, for which a signal in the green emission channel coincides with a signal in the red emission channel. Such detection is referred to as correlated or coincidence detection. The two distinct fluorophores can be excited using two different laser excitation wavelengths [18], two-photon excitation [19] or with a single laser in the special case of energy transfer (ET) dyes [20] or semiconductor nanocrystals [21,22]. Dual-channel methods allow more sensitive detection of molecular interactions than single-channel methods.

An interaction can be detected using cross-correlation analysis of the photon streams for the two emission channels. The autocorrelation amplitudes of each channel result from free proteins ($A^G$ and $B^R$) and the complex $A^GB^R$, while the cross-correlation amplitude results only from the complex $A^GB^R$.

An interaction can also be monitored by changes in the relative brightness of the two channels for fixed time-bin widths (2D-FIDA, [23]). Free $A^G$ or $B^R$ emit in "green" or "red" channel respectively, while $A^GB^R$ emits in both channels. This is evident after plotting the two-dimensional histogram of photon counts, where x and y axes correspond to the number of photon counts (for a fixed time-bin width) detected in "green" and "red" channel, respectively. The position of the free and bound species on the 2D-FIDA histogram species is along the axes and along the diagonal, respectively.

Photon Arrival-time Interval Distribution analysis (PAID) is an analytical method that is applicable to both single- and dual-channel formats (see WO 2004/011903A2). PAID uses fluorescence fluctuations to extract simultaneously coincidence, brightness, diffusion time, and concentration of fluorescently-labeled molecules diffusing in a confocal detection volume. PAID is based on recording photon arrival times, and plotting two-dimensional histograms of photon pairs, where one axis is the time interval between each pair of photons 1 and 2, and the second axis is the number of other photons detected in the time interval between photons 1 and 2. PAID is related to Fluorescence Correlation Spectroscopy (FCS) by a collapse of the PAID histogram onto the time interval axis. PAID extends auto-and cross-correlation FCS by measuring the brightness of fluorescent species. PAID measures brightness while retaining information on the temporal correlation of photons, and it was shown to match or exceed other FFS methods in the accuracy of separating free and bound species. PAID can be useful for detecting static and transient interactions in-vitro and in-vivo based on one-, two- or more color coincident detection of single molecules (or small ensembles) in a small confocal or wide-field detection volumes.

Single-molecule fluorescence spectroscopy (SMFS) is an ultra-sensitive optical method for detection and analysis of individual molecules. SMFS uses laser-excitation sources to probe individual diffusing or surface-immobilized fluorescent molecules and measure their fluorescence intensity, lifetime, anisotropy, and/or spectra, yielding information about molecular structure, interactions, and dynamics. During solution-based SMFS of dilute solutions of fluorescent species, single species are observed as fluorescence "bursts" that arise when the species diffuses through the detection volume. Often, the existence of an interaction is identified using Förster resonance energy transfer (FRET). If a molecule is labeled by a pair of complementary fluorescent probes (a donor, D; and an acceptor, A) in close proximity (2-10 nm), FRET can serve as a "molecular ruler", yielding D-A distance information. FRET has been used widely for analysis of: structure and dynamics of ensembles; single-molecules (kinetics of protein and RNA folding); DNA dynamics; rotation of molecular motors; heterogeneity/dynamics of protein-DNA complexes; and single cells (using naturally-fluorescent proteins, such as GFPs and dsRed).

Dual-channel Single Molecule Fluorescence Spectroscopy (SMFS) methods have been developed for use with ratiometric observables [24-26]. The most popular ratio recovered by dual-channel SMFS is the efficiency of Förster resonance energy transfer [27-29] (also known as fluorescence resonance energy transfer), which indicates close proximity (2-10 nm) between a pair of complementary fluorescent probes, a FRET donor and a FRET acceptor [27-29]. The relationship between the FRET efficiency and distance is shown in equation 1:

$$E = \frac{1}{1+(R/R_0)^6} \tag{1}$$

where E is the FRET efficiency, R is the donor-acceptor distance, and Ro is a constant that depends on the spectroscopic properties of the fluorophores and on the physical properties of the solution. Since the relationship of FRET and donor-acceptor distance is well-characterized, the FRET efficiency can serve as a "molecular ruler", yielding donor-acceptor distance information. If the donor and acceptor groups are on two different molecules, existence of intermolecular FRET between donor and acceptor marks the existence of an interaction between the labeled molecules.

FRET has been used widely for analysis of structure and dynamics of ensembles [27,28]; of single-molecules (kinetics of protein and RNA folding [26,30-32], and heterogeneity/dynamics of protein-DNA complexes [33,34]); and single cells (using naturally-fluorescent proteins, such as GFPs and dsRed [35].

In the current single-molecule FRET procedures where only the donor is excited directly, there are several limitations that prevent its application to quantitative analysis of simple bimolecular interactions, such as $A^{Donor}$+ $B^{Acceptor} \leftrightarrows A^{Donor}B^{Acceptor}$ (where $A^{Donor}$ is donor-labeled molecule A, and $B^{Acceptor}$ is acceptor-labeled molecule B). These limitations include the following:

Proximity constraint: FRET can be used only when donor-acceptor distances in the $A^{Donor}B^{Acceptor}$ complex are sufficiently short ($R_{Donor-Acceptor}$ is less than 6-8 nm, depending on the donor-acceptor pair) to give appreciable FRET that is distinct from donor-only species. Otherwise, low-FRET $A^{Donor}B^{Acceptor}$ species are indistinguishable from free $A^{donor}$ species. The proximity constraint limits the ability of FRET to monitor interactions, since it is difficult to satisfy in all cases, especially for large complexes or pairs of proteins of unknown structure.

Existence of non-absorbing acceptors: "dark" states and/or photobleaching of most FRET acceptors (such as the far-red fluorophores Cy5 and Alexa647) yield species with donor-only characteristics ("donor-only" peak; [25]); the species contributing to the zero peak mask species with low FRET (corresponding to large donor-acceptor distance), leading to an apparent increase of the actual free $A^{donor}$ (plus any low-FRET $A^{Donor}B^{Acceptor}$ species) population.

Interference of background and impurities: Free donor-only species emit at shorter wavelength range compared to free acceptor-only species; shorter wavelength range are more prone to buffer impurities and Raman/Rayleigh scattering, decreasing the sensitivity for the identification of fluorescent species.

Inability to detect acceptor-only species: No acceptor-only species are seen either in the absence or presence of FRET, since the direct excitation of acceptor at the wavelength of the excitation of the donor is minimized to avoid crosstalk problems.

Need for corrected FRET ratio: Currently, most smFRET studies do not concentrate on obtaining accurate distances, bur rather concentrate on observing distance changes and the kinetics of such changes. A major reason for this fact is the approximate nature of the FRET-based ratio determined by the present, single-laser excitation FRET instrumentation.

Fluorescence-fluctuation spectroscopy (FFS) methods monitor interactions and dynamics by measuring timescales of fluorescence fluctuations (fluorescence correlation spectroscopy, FCS) or amplitudes of fluorescence fluctuations (such as Fluorescence Intensity Distribution Analysis, FIDA). The fluctuations result from the diffusion of limited number of fluorescent molecules through a small detection volume. Fluctuations in one or two emission ranges can be monitored with dual emission methods being more robust. Dual emission methods require two non-interacting fluorophores with distinct emission ranges. The fluorophores are excited using two different laser-excitation wavelengths or two-photon excitation sources.

Performing the dual-channel measurements with dual-laser excitation format (as with cross-correlation FCS and certain applications of 2D-FIDA) solves some of the problems with single-laser excitation. For example, acceptor-only species are now visible and species with donor and acceptor both present with no FRET are now visible. However, new problems arise that prevent its application to quantitative analysis of certain simple bimolecular interactions, such as $A^{Donor}$+ $B^{Acceptor} \leftrightarrows A^{Donor}B^{Acceptor}$. These problems include:

Proximity constraint: Dual laser excitation cannot distinguish well between high FRET species and acceptor only species, since both only emit in the acceptor channel.

Need for corrected FRET ratio: FRET efficiency may be determined by comparing the amount of acceptor fluorescence detected to the amount of donor fluorescence detected. This is complicated, however, by the fact that the majority of the acceptor fluorescence detected comes from direct excitation. This increases the noise on the FRET-induced signal, decreasing the accuracy of FRET efficiency extracted.

SUMMARY OF THE INVENTION

The present invention overcomes several limitations of the previous methods. The present invention provides a platform for generating multiple excitation-dependent emission streams (that can be thought of as different "channels") that can be collapsed into convenient ratiometric and non-ratiometric expressions that report on information including the structure, dynamics, stoichiometry and interactions of the biomolecules of interest, such as nucleic acids, proteins, nucleotides, peptides, fluorophore-chelator conjugates, peptide nucleic acids, lipids, sugars, and hybrids of the aforementioned molecules. Thus complex mixtures of biomolecules can be easily resolved and evaluated. Parameters or information that characterize the structure, interaction, and dynamics (such as equilibrium binding constants, on- and off-rates for a bimolecular interaction, protein denaturation/renaturation kinetics, single chain conformational change, chain dynamics, conformation due to binding and nucleic-acid hybridization/melting kinetics) can be easily extracted from the emission profiles of the flurophore(s).

The present invention covers methods for analyzing a sample to determine information about one or more molecules that may be present in said sample. The method includes the step of providing a sample in a detection zone wherein the sample includes at least one molecule that is labeled with at least one fluorophore to provide a labeled molecule. The fluorphore remains within the detection zone for a detection period and is capable of emitting a signal that has properties including wavelength, intensity, lifetime and polarization. The labeled molecule is exposed to radiation within the detection zone. The radiation also has properties that include wavelength, intensity, lifetime and polarization. As a feature of the present invention, the at least one of the properties of the radiation is modulated by changing the property from an initial state to at least one subsequent state and then changing the property back from the subsequent state to the initial state. This modulation occurs over a modulation period that is equal to or less than the detection period. Modulation periods are typically less than 1 millisecond and can be 250 microseconds or less. For a change between the initial state and a single subsequent state, the modulation becomes simply an alternation between the two states; At least one of the properties of the signal emitted by the fluorophore is measured while the fluorophore is located within said detection zone to obtain an emission profile. This emission profile is then used to determine information about various molecules including both labeled and/or non-labeled molecules that may be present in the sample.

In one embodiment of the present invention, the method relies on time-division multiplexing (TDM) of various excitation beams with a period shorter than the diffusion/drift time of a molecule through the confocal excitation volume combined with burst or non-burst analysis and multi-dimensional histograms of the resulting fluorophore emissions (emission profile). Excitation wavelengths and/or excitation polarizations and/or intensities of continuous-wave or pulsed laser excitation sources can be rapidly alternated or modulated during the transit time of the molecule to maximize the information extracted by the diff-using/drifting molecule. For example, the wavelength and/or polarization of excitation can be alternated, and pulsed lasers can be used to provide time-resolved information. The emission can be examined in terms of wavelength, polarization, and excitation-emission time-interval. The statistics of the emitted photons can also be used to extract diffusion and brightness information for the species of interest. This rich multi-channel information can be represented in multi-dimensional histograms that can be simplified by use of ratiometric and non-ratiometric expressions that allow resolution and characterization of subpopulations. The use of ratiometric expressions is remarkably robust, since it provides an intensity-independent means for extracting structural information, stoichiometry and molecular interaction parameters from diffusing molecules. The ratiometric observables are not sensitive to the diffusion trajectory through the excitation volume, increasing the statistical accuracy of species classification.

In a second embodiment, the same TDM of various alternate or modulated excitation beams of a confocal excitation volume are used to interrogate immobilized molecules. In this case, the modulation period is faster than the molecular dynamics of interest, photophysics, conformational dynamics, on- or off-rates of a bimolecular interaction and similar changes between different molecular states.

In a third embodiment, TDM of various excitation beams is used for wide-field excitation (transmission, epi-illumination and total internal reflection (TIR)) in conjunction with a time-correlated photon counting imaging device of diffusing or immobilized molecules. Here again, the modulation period is faster than diffusion, molecular dynamics of interest, photophysics, conformational dynamics, on- or off-rates of a bimolecular interaction and the like. In this embodiment spatial and temporal correlation/histogramming can be performed simultaneously.

Some of the features and analysis methods can be implemented even without TDM for unique dyes such as ET dyes and semiconductor nanocrystals that can emit at separate wavelengths upon excitation from a single excitation source. The coincidence detection and data analysis using ratiometric expressions can still be performed even without TDM.

The present invention provides for the analysis of macromolecular interactions and macromolecular structure in small detection volumes or zones and at low molecule concentrations (up to about 10 molecules per detection volume) and at higher molecule concentration (greater than 10 molecules per detection volume). Applications for the present invention include diagnostics, drug discovery, in-vitro and in-vivo high-throughput-screening, gene expression studies and target validation. The methods of the present invention can detect static and transient interactions (such as protein-protein, protein-nucleic acid, protein-drug, and nucleic acid-nucleic acid interactions) based on site-specific fluorescence labeling, rapid alternation of laser excitation sources (on timescales faster than diffusion for diffusing molecules, as well as on timescales faster that drift or molecular dynamics for immobilized molecules) and analysis of photons streams emanating from species diffusing (or flowing) in small detection volumes. The present invention represents an unusually flexible platform that can be extended to additional excitation sources, fluorophores, excitation schemes and ratiometric expressions to thereby increase the reliability and information content of biomolecular analysis.

The above discussed and many other features and attendant advantages of the present invention will become better understood by reference to the detailed description when taken in conjunction with the accompanying drawings.

DETAILED DESCRIPTION OF THE INVENTION

Figure 1:
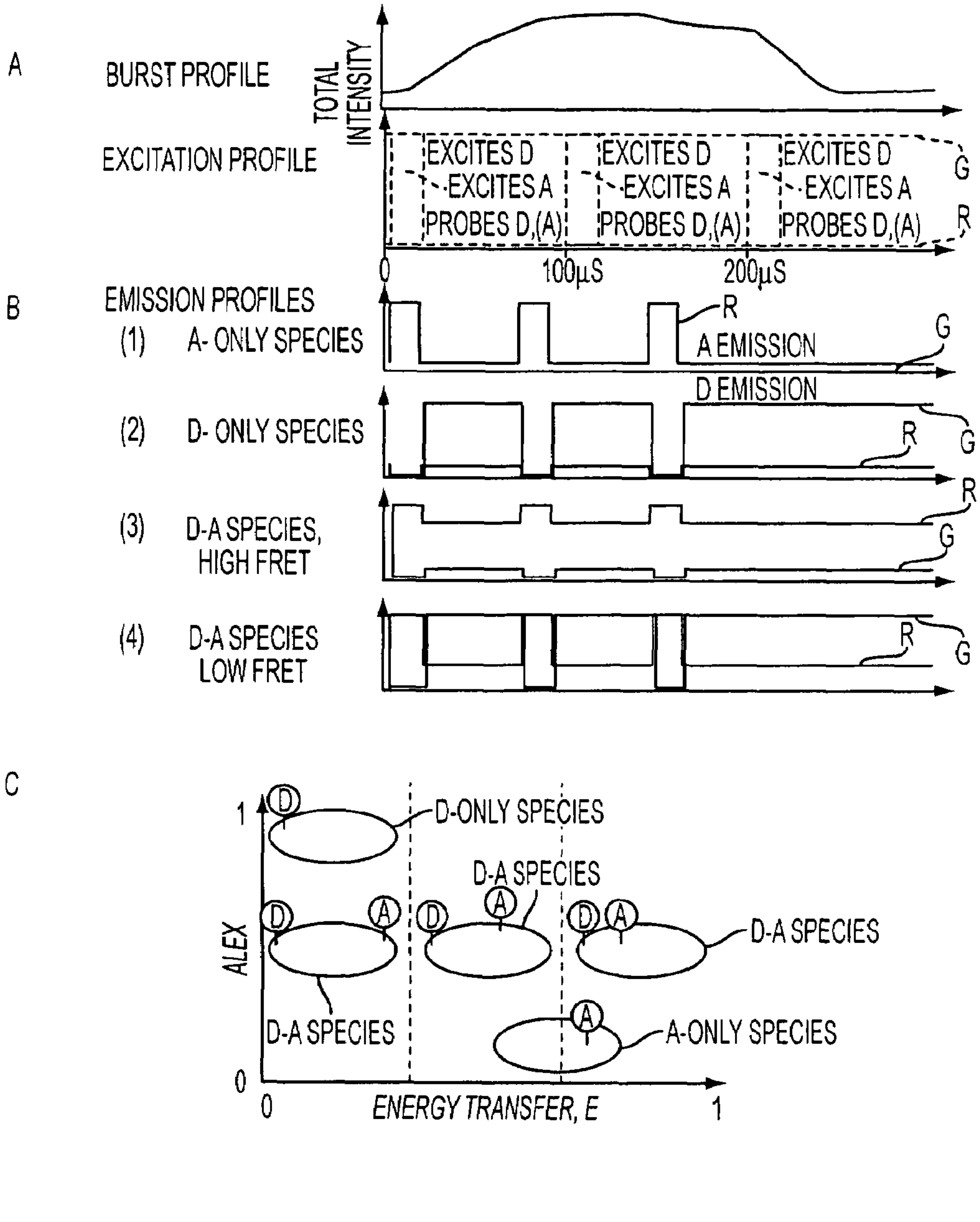
FIG. 1A shows an exemplary burst and excitation profile for two alternating laser beams wherein one beam excites the donor fluorophore directly and probes the acceptor fluorophore indirectly via Förster resonance energy transfer and the second beam excites the acceptor fluorophore.
FIG. 1B shows exemplary emission profiles for the acceptor (A) and donor (D) fluorophores when the fluorophores are attached alone or in combination on a species.
FIG. 1C diagrammatically depicts an exemplary two-dimensional histogram that is derived from the exemplary emission profiles shown in FIG. 1B where the E axis sorts species in terns of the interprobe distance $R_{D\text{-}A}$ to provide structural information and the ALEX axis sorts the species in terms of D-A stoichiometry and the relative molecular brightness.

One embodiment of the present invention provides an additional dimension to smFRET and/or cross-correlation that allows analysis of samples of great heterogeneity and quantitates molecular interactions with high sensitivity. This is performed by modifying the original single-laser excitation FRET to implement an alternate-laser-excitation (ALEX) scheme (FIG. 1). Specifically, ALEX-FRET is based on rapid alternation between two laser excitations (FIG. 1A) at timescales faster (greater than 10-fold faster) than the diffusion of the molecules of interest through femtoliter confocal-detection volumes (0.2-1 ms). In accordance with this embodiment of the present invention, the first laser probes the FRET donor in a direct fashion and the FRET acceptor in an indirect, FRET-dependent fashion. The second laser probes the FRET acceptor in a direct, FRET-independent fashion. This double probing yields emission profiles that allow differentiation between donor-only, acceptor-only, and donor-acceptor species characterized by various donor-acceptor distances. The emission profiles may be summarized in 2-D histograms of two ratiometric expressions: the FRET-based E ratio, and an ALEX-based S ratio described below. The individual species are identified using "burst analysis", a routine analysis that identifies individual diffusing molecules as short spikes of fluorescence photons over a dark background ([36] U.S. Pat. Nos. 6,137,584 and 6,208,815).

Within a burst (FIG. 1A), the first laser (denoted D for "Donor" excitation; dotted line "G", FIGS. 1A, 3) excites the donor directly, and probes the acceptor indirectly and only if $R_{Donor\text{-}Acceptor}$ is within FRET range ($R_{Donor\text{-}Acceptor}$ less than 60-90 Å, depending on the donor-acceptor pair). The second laser (denoted A for "Acceptor" excitation; dotted line "R") excites the acceptor fluorophore directly. Dividing the time axis into intervals i whose durations match the laser excitation modulation period Δt, the donor-excitation-dependent donor-emission is written $F_i^{dD}$ (D is for "Donor" emission; solid line "G", FIG. 1B for 0-50, 100-150, and 200-250 μs) and the donor-excitation-dependent acceptor-emission is written $F_i^{dA}$ (A is for "Acceptor" emission; solid line "R", FIG. 1B for 0-50, 100-150, and 200-250 μs). A burst is defined as a contiguous series of modulation periods, where the index i runs from $i_0$ to $i_0+n-1$, where n is the number of periods that make up the burst. The fluorescence from a burst is written:

$$F_{burst}^{dD} = \sum_{i=i_0}^{i_0+n-1} F_i^{dD}$$

$$F_{burst}^{dA} = \sum_{i=i_0}^{i_0+n-1} F_i^{dA}$$

$F_{burst}^{dA}$ and $F_{burst}^{dD}$ allow us to calculate proximity ratio E (simplified expression of FRET efficiency) that provides $R_{Donor\text{-}Acceptor}$ information:

$$E_{burst} = \frac{F_{burst}^{dA}}{F_{burst}^{dA} + \gamma F_{burst}^{dD}} \quad (2)$$

The factor γ is a detection correction factor defined as $\gamma=(Q_A\eta_A)/(Q_D\eta_D)$, where $Q_D$ and $Q_A$ are the quantum yields of the donor and the acceptor, and $\eta_D$ and $\eta_A$ the detection efficiencies of the donor- and acceptor-emission channels [25]. The E ratio assumes very low values for donor-only species ($2^{nd}$ timetrace, FIG. 1B; E value reflects a small donor-emission in the acceptor-emission range, typically 5-10%), low values for donor-acceptor species with $R_{Donor\text{-}Acceptor}$ greater than $R_{0,Donor\text{-}Acceptor}$ (distances significantly longer than the optimal dynamic range of FRET; $3^{rd}$ timetrace, FIG. 1B), and high values for donor-acceptor species with $R_{Donor\text{-}Acceptor}$ less than $R_{0,Donor\text{-}Acceptor}$ ($4^{th}$ timetrace of FIG. 1B). Moreover, acceptor-only species cannot be observed easily, since the acceptor is not efficiently excited at the donor-excitation wavelength ($1^{st}$ timetrace, FIG. 1B). Since E depends only on donor-excitation-dependent emission, it is not affected by the alternation period, intensity ratio, or duty cycle of the lasers used for ALEX.

Alternatively, the data can be analyzed by bins of the modulation period duration, where only bins belonging to valid bursts are analyzed:

$$E_i = \frac{F_i^{dA}}{F_i^{dA} + \gamma F_i^{dD}} \quad (3)$$

The second laser (denoted a) excites the acceptor directly. It does not excite the donor at all. The existence of the second laser allows the formulation of the ALEX-based ratio S (or ALEX) that provides donor-acceptor stoichiometry of a species. We define $ALEX^d$ as the fraction of the donor-excitation-dependent emissions over the sum of donor-excitation- and acceptor-excitation-dependent emissions:

$$ALEX_{burst}^d = \frac{F_{burst}^{dA} + \gamma F_{burst}^{dD}}{F_{burst}^{dA} + \gamma F_{burst}^{dD} + F_{burst}^{aA}} \quad (4)$$

$F_{burst}^{dA}+\gamma F_{burst}^{dD}$ is the sum of all donor-excitation-dependent emissions in a burst, $F_{burst}^{aA}$ is the acceptor-excitation-dependent acceptor-emission (solid line "R", FIG. 1B for 50-100, 150-200, and 250-300 μs) in a burst. The term $F^{burstaD}$ (solid line "G", FIG. 1B for 50-100, 150-200, and 250-300 μs) is a negligible term reflecting the fact that the donor is not excited at the acceptor-excitation wavelength, and can be excluded safely from the analysis (verified experimentally). An equivalent expression is $ALEX_{burst}^a$, which is the fraction of the acceptor-excitation-dependent emissions over the sum of donor-excitation and acceptor-excitation-dependent emissions. In the following description we use $ALEX_{burst}^d$ for all calculations, but rename it to the general term ALEX Significantly, ALEX assumes distinct values for distinct species present in mixtures of interacting components (FIG. 1B). Assuming that $$F_{burst}^{dA}+\gamma F_{burst}^{dD}=F_{burst}^{aA} \quad (5)$$

for species containing a single donor and a single acceptor (achieved by adjusting the ratio of excitation intensities), ALEX for donor-only species (2nd timetrace, FIG. 1B) assumes high values, close to 1 (reflecting that $F_{burst}^{aA}=0$). On the other hand, ALEX for acceptor-only species (1st timetrace, FIG. 1B) assumes low values, in the 0-0.2 range; these values reflect the fact that $F_{D,exc}$ has a small value due to the small direct acceptor-excitation at the donor-excitation wavelength. Finally, ALEX for donor-acceptor species characterized by any donor-acceptor distance (3rd and 4th timetraces of FIG. 1B) assumes intermediate values, in the 0.4-0.8 range. The distance-independent nature of ALEX is due to the distance-independent nature of $F^{dD}$. Upon donor-excitation with light of excitation intensity $I^{dD}$ at a wavelength where donor has extinction coefficient $\epsilon^{dD}$, the terms that make up $F^{dD}$ are:

$$F_i^{dD}=I_d\epsilon_{dD}Q_D\eta_D(1-E)\Delta t \text{ and } F_i^{dA}=I_d\epsilon_{dA}Q_A\eta_A E\,\Delta t \quad (6)$$

Note that the sum $$F_{burst}^{dA}+\gamma F_{burst}^{dD}=I_d\epsilon_{dA}Q_A\eta_A E\Delta t+\gamma I_d\epsilon_{dD}Q_D\eta_D(1-E)\Delta t=I_d\epsilon_{dA}Q_A\eta_A\Delta t \quad (7)$$

is independent of FRET. Since ALEX is an expression of FRET-independent intensities $F_{burst}^{dA}+\gamma F_{burst}^{dD}$ and $F_{burst}^{aA}$, it is also independent of E, and independent of $R_{Donor-Acceptor}$. The $F_{burst}^{aA}$ provides a low-background wavelength range for identification of acceptor-containing species through search algorithms that identify individual bursts ("burst-analysis"; [37,38]), allowing detection of static heterogeneity, as well as monitoring of interactions by simple counting of A-only and donor-acceptor species upon the titration of acceptor-only species with increasing concentrations of donor-species. Moreover, ALEX is sensitive to changes in the molecular brightness $q_D$ ($q_D=\epsilon_{dD}Q_D$) of a diffusing species. Changes in brightness might arise from a) changes in the number of donors of a diffusing species (e.g. a donor-acceptor species vs. a donor$_2$-acceptor species, as a result of oligomerization); or b) changes in the local environment of the donor (allowing discrimination of distinct conformations). Combination of E and ALEX on two-dimensional histograms allows sorting and quantitation of reactants and products of a reaction/interaction, and identifies structural features of the products that can determine the specificity of an interaction. Information about diffusion time, brightness, and concentration can also be extracted from the burst search analysis.

The ALEX calculation in (5) is equivalent to the E calculation in (2). ALEX can also be calculated similarly to the way E is calculated and displayed in (3) and (4) i.e. by modulation bins, or by averaged modulation bins per burst.

Note that in the ALEX-FRET diffusion embodiment described above, we measure: $F_{burst}^{dD}$, $F_{burst}^{dA}$, $F_{burst}^{aD}$ (generally 0), and $F_{burst}^{aA}$. From burst-search analysis, one can determine the total corrected photon counts for a burst $S=F_{burst}^{dA}+\gamma F_{burst}^{dD}+F_{burst}^{aA}$, the burst duration $\tau_{burst}$, and the time between bursts T. A multi-dimensional histogram can be constructed from these 7 burst quantities and subpopulations can be identified and separated. It is often beneficial to collapse these parameters into fewer ratiometric expressions or histogram axes, as it is the case with E and ALEX. Another ratio that can be used to obtain information is to average photon emission rate per burst:

$$ER = \frac{S}{\tau_{burst}}.$$

As shown below, other modulation schemes such as polarization modulation, intensity modulation (triplet/saturation) and short interlaced pulsed-laser excitation, can generate many more observables and ratiometric expressions.

Figure 2:
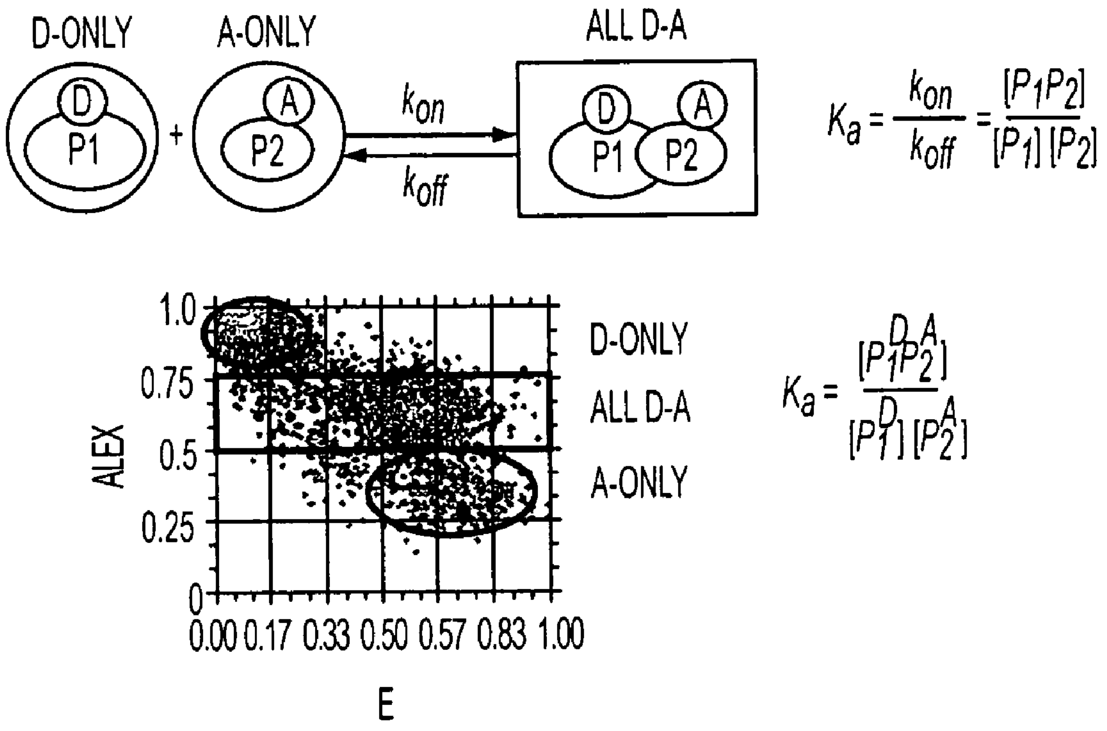
FIG. 2 is a diagrammatic representation of an exemplary method in accordance with the present invention for analyzing a bimolecular association reaction between two molecules (P1 and P2) wherein P1 is labeled with a donor fluorophore and P2 is labeled with an acceptor fluorophore. An exemplary histogram is shown that is used in determining properties of the reaction product and properties of the equilibrium between the D-only, A-only, and D-A species

The present invention yields simultaneously distance and stoichiometry information, obtained from the E and ALEX axis of the E-ALEX two-dimensional histogram. It can be used to monitor interactions. Binding is indicated by presence of donor-acceptor ALEX values. Frequency of events in each subpopulation, the photon bursts can be extrapolated to concentrations, which are then used to calculate the dissociation constant $K_d$=[A][B]/[AB]. This is described schematically in FIG. 2. Direct observation of all the species involved in a bimolecular association reaction allows the direct or indirect extraction of the thermodynamic and kinetic constants that characterize a chemical equilibrium.

The present invention does not require complex modeling and fitting required in several FFS methods. The data can be analyzed with simple Gaussian fitting, providing direct information within seconds of data acquisition. A more accurate model for fitting can be derived from shot-noise analysis; or the E histogram, a beta function fits the histogram better than a Gaussian.

Analysis of the fluorophore emissions spectra or signal is not limited to the burst analysis methods described. FFS methods, especially PAID, can be extended to account for the additional information available using the ALEX-FRET-based method of the present invention. Due to better accounting of background and multi-molecular events, such extensions of FFS methods will provide more accurate determination of concentrations and background.

Examples of practice are as follows:

EXAMPLE 1

DNA Model Systems

Figure 3:
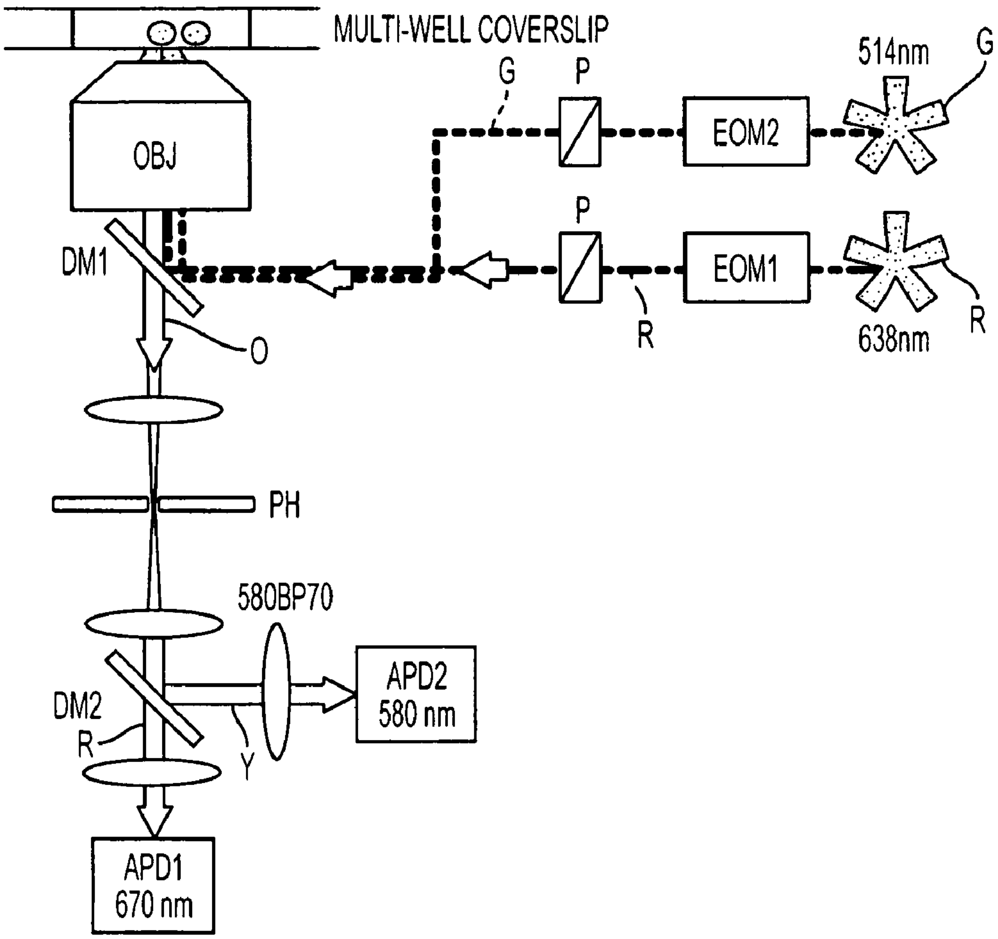
FIG. 3 is a diagrammatic representation of an exemplary ALEX-equipped confocal fluorescence microscope system for carrying out the methods of the present invention. "G", "R", "O" and "Y" denote the colors green, red, orange and yellow, respectively. OBJ=microscope objective; PH=pinhole; EOM=electrooptical modulator; DM=dichroic mirror; P=polarizer; LP=long pass filter and APD=avalanche photodiode. The 514-nm line of an $Ar^+$ laser (dotted line G) and the 638-nm of a diode laser (dotted line R) are coupled to fiber optics and used to excite the sample of interest. Fluorescence from the various species is (line O) is collected through the objective, spatially and spectrally filtered and photon-arrival times recorded by the APDs.

Using the instrumentation shown in FIG. 3, the ability of the present invention to resolve species containing different numbers of donors and acceptors (and to recover $R_{Donor\text{-}Acceptor}$) was explored by studying fluorescently-labeled DNA fragments carrying donor and acceptor probes separated by approximately 4, 7, and 11 nm, corresponding respectively to high, low and zero-FRET species (FIG. 4A) [39]. 35 base pair DNA fragments were prepared by total synthesis using known-procedures. The sequence of the top strand was similar to one used in Ref. 25 with modifications that ensured identical local environment for the fluorophores used in each sample. We incorporated amino-dT residues (Glen Research, Sterling, Va.) at positions 1 or 5 of the top strand. The sequence of the bottom strand was complementary to the top strand. We incorporated amino-dT residues at positions 10, 20, or 30 of the bottom strand. Trityl-ON DNA fragments were HPLC-purified using a C2/C18 µRPC column (APB, Piscataway, N.J.) on an ÄKTA Purifier (APB), and were labeled with amine-reactive N-hydroxy-succinimidyl-esters of Alexa647, Alexa532, tetramethyl-rhodamine (TMR) (Molecular Probes, Eugene, Oreg.) or Cy3B (APB) using manufacturer's instructions. Labeled DNA fragments were HPLC-purified as trityl-ON DNA fragments. Double-stranded DNA was formed by hybridization of complementary strands in annealing buffer [10 mM HEPES-NaOH (pH 7.0), 500 mM NaCl, 1 mM EDTA, and 5% glycerol) and stored at −20° C. Hybridization was performed using a 50% molar excess of D-containing bottom DNA strand to ensure that all A-only strands were hybridized (this was verified using non-denaturing gel electrophoresis).

Figure 4:
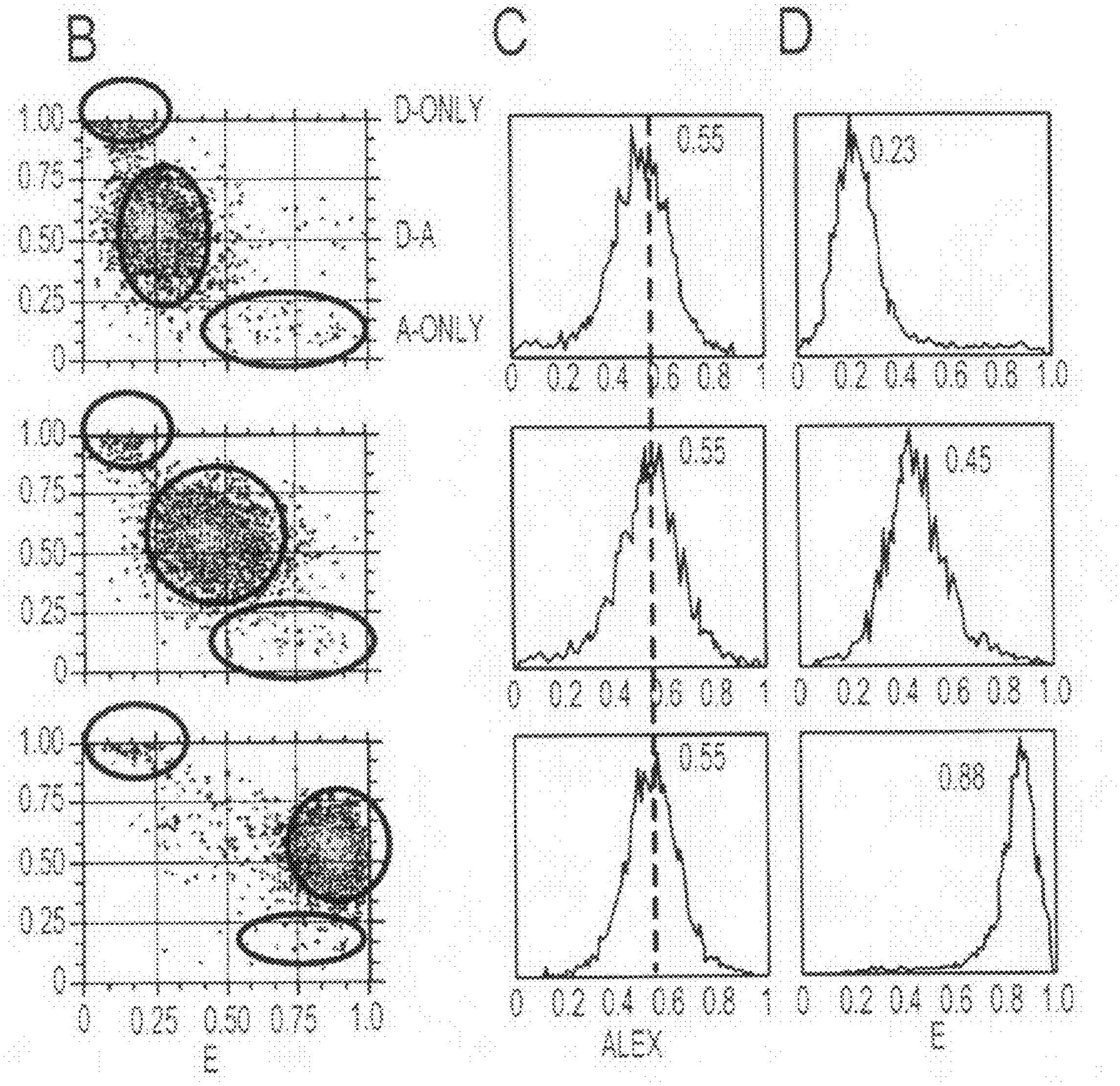
FIG. 4A is a diagrammatic representation of donor and acceptor fluorophores located on DNA fragments at distances of 4 nm, 7 nm and 11 nm from each other.
FIG. 4B depicts the two-dimensional histograms (E-ALEX) derived using the method of the present invention for the three-labeled DNA fragments shown in FIG. 4A.
FIG. 4C depicts one-dimensional (ALEX) histograms derived in accordance with the present invention for the three-labeled DNA fragments shown in FIG. 4A.
FIG. 4D depicts one-dimensional (E) histograms derived in accordance with the present invention for the three-labeled DNA fragments shown in FIG. 4A.
Figure 4A:
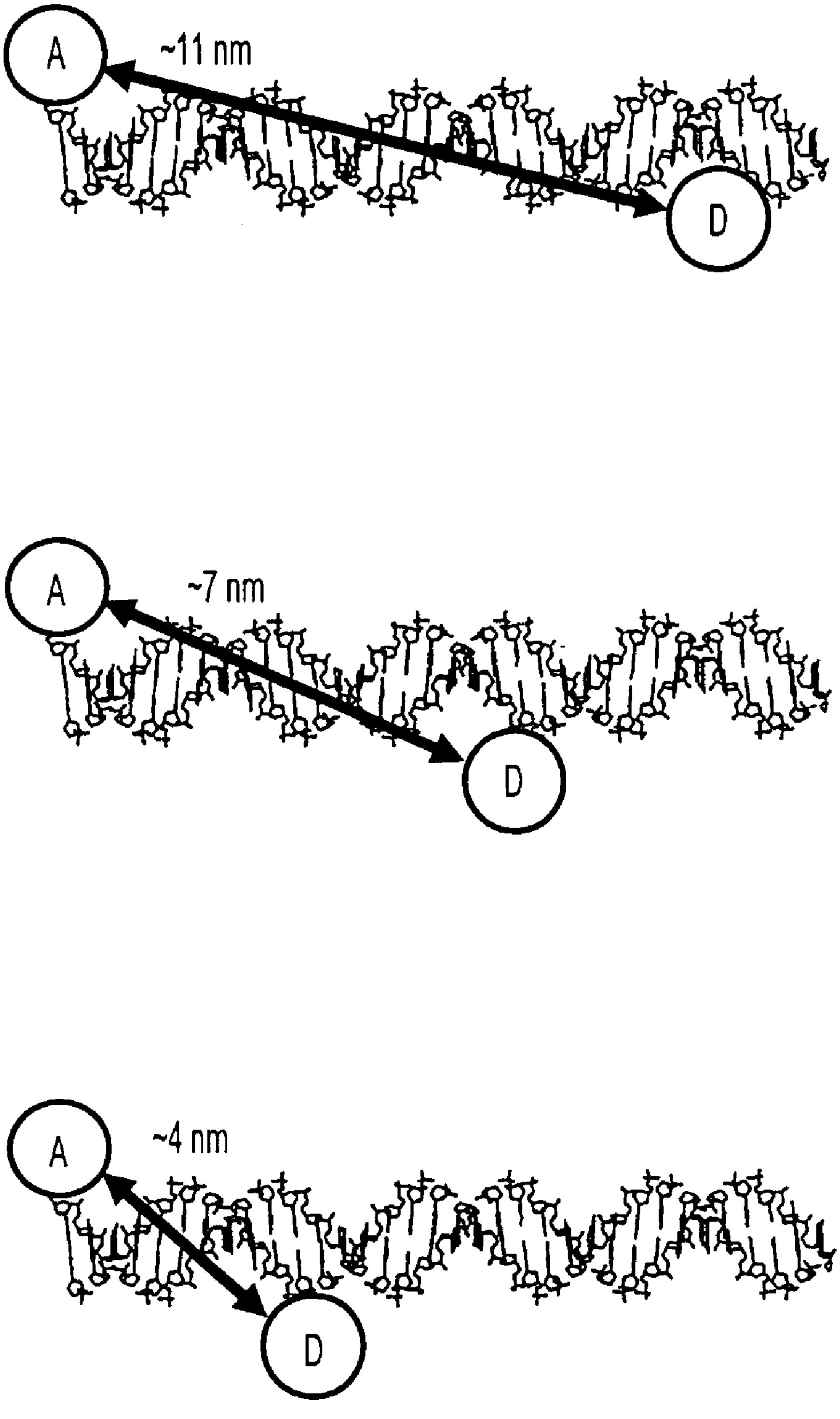
Figure 5:
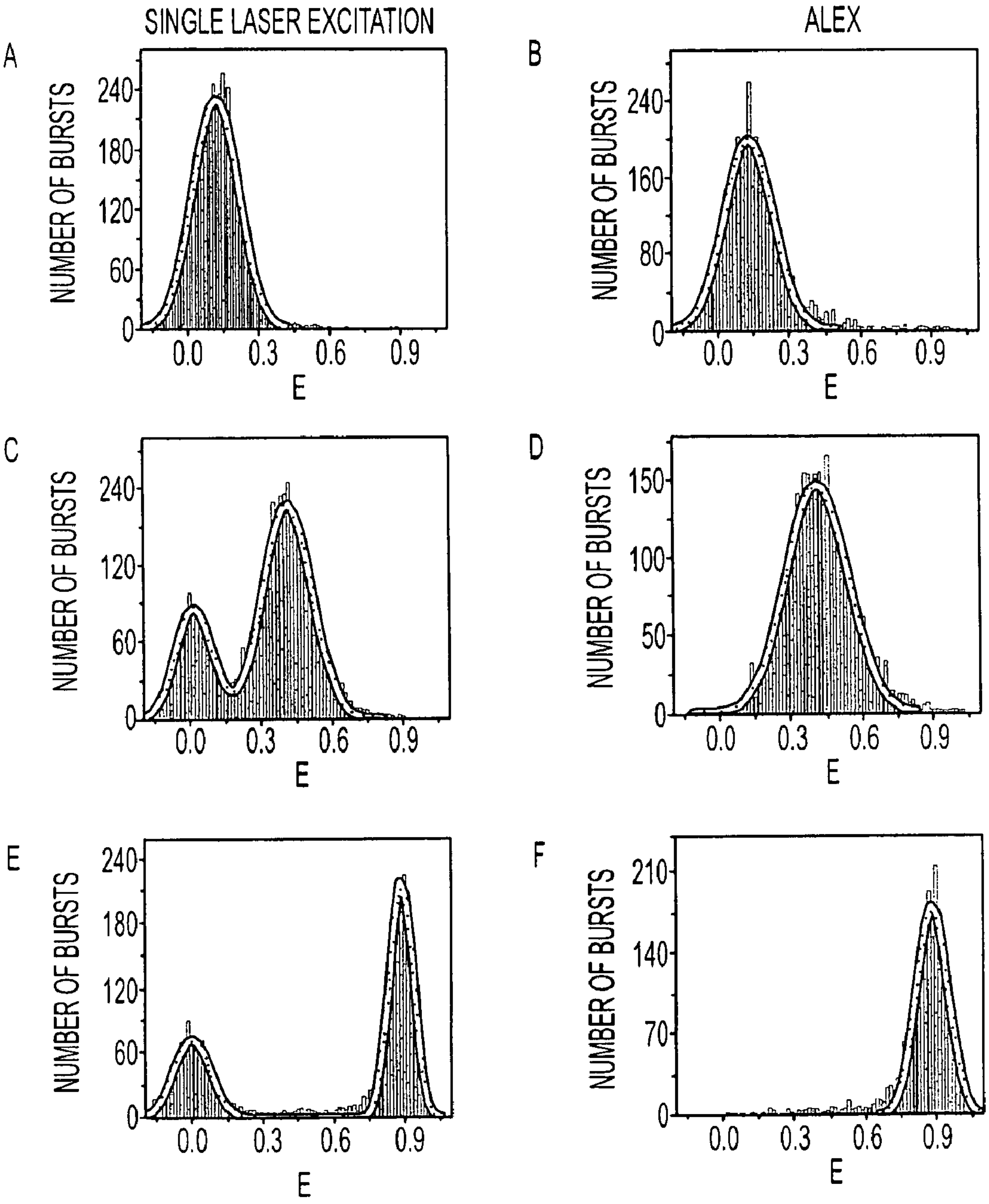
FIGS. 5A, 5C and 5E depict E histograms obtained using a single laser excitation method.
FIGS. 5B, 5D and 5F depict E histograms obtained using the alternating-laser excitation method in accordance with the present invention. Use of alternating-laser excitation eliminates the artifactual peak centered around E=0.

For the "high-FRET" DNA, there was a clear separation of donor-acceptor species from donor-only and acceptor-only species. The donor-acceptor species showed high FRET and intermediate ALEX. This was also reflected in the individual, collapsed ALEX and E histograms. Moving the acceptor further away from the donor (as in low-FRET DNA) does not change the ALEX ratio of donor-acceptor species, but lowers the E between them (FIG. 4B, middle panel). Moving the acceptor even further away from the donor (as in zero-FRET DNA), did not change the ALEX ratio of donor-acceptor species, but lowered the E between them even further. Upon correction of E values for non-FRET contributions, the extracted donor-acceptor distances corresponded well to the distances expected from the 3-dimensional structure of DNA and the position of the fluorophores. ALEX appears to be is entirely independent of E, and ALEX-FRET allows reliable corrections of E using internal standards (donor-only and acceptor-only species) present in every sample used for single-molecule measurements. The independence of ALEX with respect to E means that the ALU-E histogram has two orthogonal axes which is a useful property for subpopulation separation.

ALEX-FRET was performed using variable excitation-intensity ratios. E was independent of laser excitation intensities; variable excitation-intensity ratios causes drastic changes in the ALEX of acceptor-only and donor-acceptor species. Changing the laser-excitation duty cycle produced equivalent results. The easy control of the excitation-intensity ratio allows a "zoom-in" in the ALEX area of interest. For example, in order to maximize resolution, analysis of acceptor-containing species can be performed with the midpoint between acceptor-only and donor-acceptor species placed at an ALEX-based ratio of approximately 0.5. This ability is particularly useful for analysis of complexes containing multiple donor and acceptors.

Alternation periods $\tau_{Alt}$ of 20-3000 µs (compared with transit time of approximately 400 µs for the DNA fragments used) were examined. Changes in alternation periods did not change the E of donor-acceptor species (mean E approximately 0.45). Increasing $\tau_{Alt\,from}$ 20 to 250 µs caused minimal changes in ALEX for donor-acceptor species, but further increase to 3000 µs caused large changes, especially in the width of the ALEX distribution. This reflects the effect of diffusion of donor-acceptor species on ALEX. This example defines a working range of $\tau_{Alt}$ that eliminate effects of diffusion on the width of ALEX distributions. The low $\tau_{Alt}$ limit is determined by the EOM response time (approximately 2 µs). Periods as short as 10 µs can be used without loss of ALEX resolution, allowing analysis of fast-diffusing/flowing species characterized by smaller size and hydrodynamic volume. The high $\tau_{Alt}$ limit is determined by diffusion time, $\tau_D$. The relationship between $\tau_D$ and ALEX width might be used to extract diffusion times of species resolved by ALEX-FRET. These limits of alternation-period apply for the version of ALEX-FRET that utilizes continuous-wave laser excitation sources for alternation. However, the alternation period can become much faster (down to about 10 ns) by using alternation pulsed laser excitation sources (as described below).

The artifactual "donor-only" peak contaminates all single-molecule FRET experiments [25]. To show the ability of ALEX-FRET to identify and remove the donor-only peak, we conducted single-laser excitation (SLEX) and ALEX-FRET measurements on donor-acceptor DNA fragments with variable E. Analysis of DNA fragments characterized by low or zero FRET demonstrates best the need for removing the donor-only peak, since the E distribution of donor-acceptor species overlaps significantly or merges completely with the E distribution of donor-only species, thwarting quantitation of bursts or accurate evaluation of E. The SLEX-based E histogram for such a DNA fragment (FIG. 5A) showed only a single apparent low-E species (0.22±0.15), without separation of donor-acceptor and donor-only species. The ALEX-based E histogram for donor-acceptor species in accordance with the present invention (FIG. 5B) showed a single low-E species (0.23±0.15), distinct from donor-only species in terms of E (0.23 vs 0. 15). Removal of the donor-only peak allowed a reliable donor-acceptor distance measurement, something not possible for a SLEX-based measurement of this sample. Removal of donor-only peak simplifies the analysis of donor-acceptor species with different E values, since the full E range is accessible for distance measurements, and E can be recovered with great accuracy. This allows differentiation between species characterized by small $R_{donor\text{-}acceptor}$ differences ($\Delta R_{donor\text{-}acceptor}$ equal to about 5 or less), such as donor-acceptor labeled DNA where the donor and acceptor are separated by 15, 16, and 17 bp respectively. The ability to recover accurate E (standard error of mean equal to about 0.01) allows reliable measurements of $R_{donor\text{-}acceptor}$ or $\Delta R_{donor\text{-}acceptor}$, even for $R_{donor\text{-}acceptor}$ much greater than $R_{0,\ donor\text{-}acceptor}$, facilitating the design of labeling schemes for probing distances and interactions in large multi-component complexes. Additional examples of rejection of D-only peak is shown in FIGS. 5C-F.

Removal of the variable donor-only peak provided by the present invention is also a key process in converting smFRET into a quantitative tool for analysis of interactions. ALEX-FRET increases the generality of smFRET, since it relaxes the proximity-constraint of SLEX for identifying interactions, allowing even species of 0% E (which corresponds to donor-acceptor distances as large as the dimensions of the excitation spot itself (approximately 300 nm-approximately 1 µm for a typical confocal volume using visible-light excitation and a high-NA objective). The detection zone or spot can have dimensions as small as 50 nm and as large as 20 µm, if desired. The volume of the detection zone will usually be below 100 femtoliters.

Figure 6:
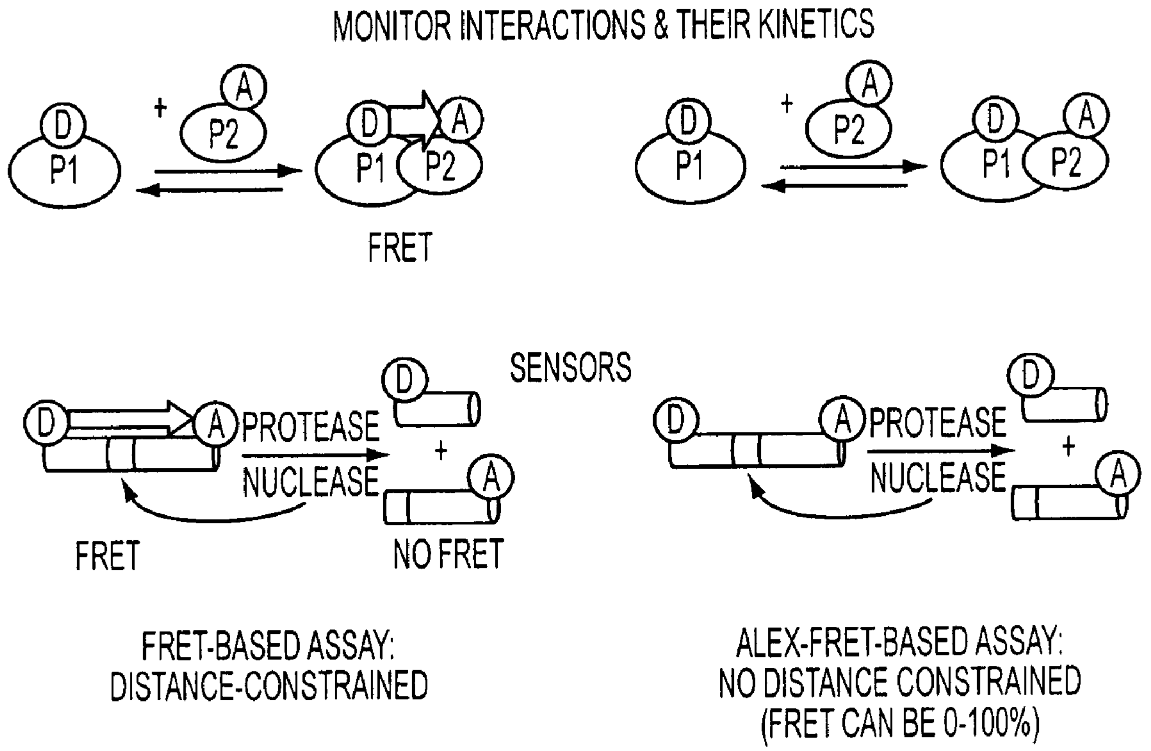
FIG. 6 is a diagrammatic representation showing that the alternating laser excitation method of the present invention is not constrained by the distance between the donor and acceptor fluorophores.

The distance-independent nature of ALEX-FRET is outlined in FIG. 6. When donor ("D") and acceptor ("A") fluorophores are respectively attached to two molecules that interact, the emission signals from the complex, while traversing the confocal spot, are coincident (i.e. "co-localized" in time and (confocal) space). Coincidence and/or cross-correlation analysis can identify the "bound" species. This is critical in cases of biomolecules of unknown structure (such as the thousands of gene products identified by genomic-DNA sequencing) or when site-specific labeling is not practical or may affect the activity of the macromolecule.

To show the ability of ALEX-FRET to resolve mixtures and measure their components accurately, we prepared an equimolar mixture of DNA fragments showing different E (a "low-E", and a "high-E" DNA). The bursts were generated using the $F^{aA}$ threshold (direct acceptor-excitation. Using the E histogram for the donor-acceptor species, two major species were seen, reflecting the donor-acceptor species of the individual DNA components. Using a 2-Gaussian fit, the ratio of the (Low-E/High-E) bursts was approximately 1.03:1, in excellent agreement with the expected concentration ratio. The recovered means and widths of E are within 5% of the ones measured for individual components. Similar experiments on 1:2 and 2:1 Low-E:High-E mixtures yielded similar results. The results show that the method of this embodiment of the present invention (ALEX-FRET) can resolve and quantitate species with comparable diffusion times.

EXAMPLE 2

Monitoring Oligomerization

Several protein interactions are characterized by oligomerization of one or more of the interacting components. For example, most transcription factors oligomerize and bind to DNA with variable protomer:DNA stoichiometries. The ALEX ratio is sensitive to the ratio of the number of green fluorophores per complex (equivalent to donor fluorophores in the case of FRET) to the number of green fluorophores per complex (equivalent to acceptor fluorophores in the case of FRET). Specifically, for molecules with fluorophore stoichiometries 'green'$_2$-'red', 'green'-'red', and 'green'-'red'$_2$ (separated by a large distance, E=0), the order: ALEX ('green'$_2$-'red')>ALEX('green'-'red')>ALEX('green'-'red'$_2$) applies. In this example, we evaluated the ability of the present invention to monitor oligomerization by comparing a DNA fragment carrying one 'green' (Alexa532) and one 'red' (Alexa647) with a DNA fragment carrying two 'green' and one 'red'. The E-ALEX histograms for the two DNA fragments are distinct along the ALEX axis. The difference between the mean value of ALEX for 'green'$_2$-'red' and 'green'-'red' species is close to the maximum ALEX difference of approximately 0.16 ALEX units. We also analyzed a 1:1 mixture of 'green'$_2$-'red' and 'green'-'red' species. Using a constrained 2-Gaussian fit, we recovered a ratio of 'green'-'red':'green'$_2$-'red' bursts of approximately 0.9:1, within approximately 10% of the expected 1:1 ratio. This demonstrates that after characterizing the monomeric and dimeric (or oligomeric) form of a dimerizing system, one can extract the ratio of 'green'-'red' and 'green'$_2$-'red' concentrations as a function of donor concentration, and therefore define the dimerization binding constant.

EXAMPLE 3

Resolving Mixtures of Species with Simulated Variable Environment of the Fluorophores The E-ALEX histogram is also sensitive to differences in the brightness and emission spectra of the donors present in donor-acceptor (or 'green'-'red') species. This is important for species labeled by fluorophores with emissions that are not fully resolved. It also allows the differentiation between species of the same composition that experience different local environments that affect molecular brightness (by quenching or photo-brightening). To demonstrate this ability, we prepared 3 DNA fragments, each with a different donor (TMR, Alexa532, or Cy3B), but identical acceptor (Alexa647), separated by the same distance (approximately 7 nm). The fragments were analyzed in the same manner as Example 1. The results show marked E and ALEX differences between samples with the different donors. The discrimination along both E and ALEX axes allows increased resolution of species using double 2D-Gaussian fitting routines. Better fitting routines are also possible based on shot-noise analysis. Overall, the ability to use fluorophores with closely-spaced excitation/emission spectra provides flexibility in choosing the right fluorophore for a particular assay. For example, the TMR→Al647 pair is superior in providing donor-acceptor distance information, whereas the Al532→Al647 pair is characterized by narrower distributions that allow better resolution between species with small differences along the E and/or ALEX axes. This capability can be exploited to build sensors of subtle changes on the protein surface that arise as a result of side-chain modification (e.g. phosphorylation), which is important for signal transduction mechanisms.

EXAMPLE 4

Accurate Donor-Acceptor Distance Measurement

As mentioned above, the proximity ratio E most frequently used for FRET measurement serves only as a qualitative index of a donor-acceptor distance. Information about distances within proteins, protein-DNA and protein-protein complexes provide additional important structural information that complements that of molecular affinity, and can help define and characterize isomers impossible to observe using FFS methods. In order to extract accurate donor-acceptor distances, accurate determination of E is required. To achieve this goal, two major corrections for the measured E are required:

1) subtraction of the FRET-contaminating contributions: donor emission at the emission wavelength of the acceptor ("leakage" or "cross-talk"), direct excitation of the acceptor by donor-excitation laser, and background. Such corrections usually require separate single-molecule measurements of donor-only and acceptor-only standards.

2) consideration of instrumental correction factors (excitation and emission correction factors). The emission correction factor is defined by the quantum yields of the donor and the acceptor fluorophores, and the detection efficiencies of their emission channels. Inaccuracies in the measurement of the emission correction factor are directly reflected in inaccuracies of the E measurement.

The present invention provides ways to perform such corrections by using inherently-present donor-only and acceptor-only species as internal standards, allowing all corrections to be made using a single measurement of the sample of interest. This is significant, since it minimizes potential differences because of loss of material on surfaces on the measurement chamber and pipetting devices, pipetting errors, drift, sample positioning, as well as tedium and time associated with preparation and measurement of donor-only or acceptor-only standards. Such procedures for a limiting case that requires balancing of excitation intensities and knowledge of the emission correction factor are described in Refs. 24, 25, and 40. However, it is possible to move to more general approaches to calculate E. The present invention, however, provides a systematic way to measure the emission correction factor. Equation (2) can be rewritten as:

$$ALEX = \frac{F_{burst}^{dA} + F_{burst}^{dD}}{F_{burst}^{dA} + F_{burst}^{dD} + F_{burst}^{aA}} = \frac{I_d\varepsilon_{dD}Q_A\eta_A E + I_d\varepsilon_{dD}Q_D\eta_D(1-E)}{I_d\varepsilon_{dD}Q_A\eta_A E + I_d\varepsilon_{dD}Q_D\eta_D(1-E) + I_a\varepsilon_{aA}Q_A\eta_A} = \frac{1+(\gamma-1)E}{1+(\gamma-1)E+\beta\gamma} \tag{8}$$

$$\text{where } \gamma = \frac{Q_A\xi_A}{Q_D\xi_D} \text{ and } \beta = \frac{I_a\varepsilon_{aA}}{I_d\varepsilon_{dD}}.$$

We defined another measurable term, uncorrected E ($E_{unc}$):

$$E_{unc} = \frac{F_{burst}^{dA}}{F_{burst}^{dD} + F_{burst}^{dA}} = \frac{I_d\varepsilon_{dD}Q_A\eta_A E}{I_d\varepsilon_{dD}Q_D\eta_D(1-E) + I_d\varepsilon_{dD}Q_A\eta_A E} = \frac{\gamma E}{1+(\gamma-1)E} \tag{9}$$

From these two relations, equation (8) and (9), equation (10) is derived by removing E.

$$\frac{1}{ALEX} = 1 + \beta\gamma - \beta(\gamma-1)E_{unc} \tag{10}$$

Figure 7:
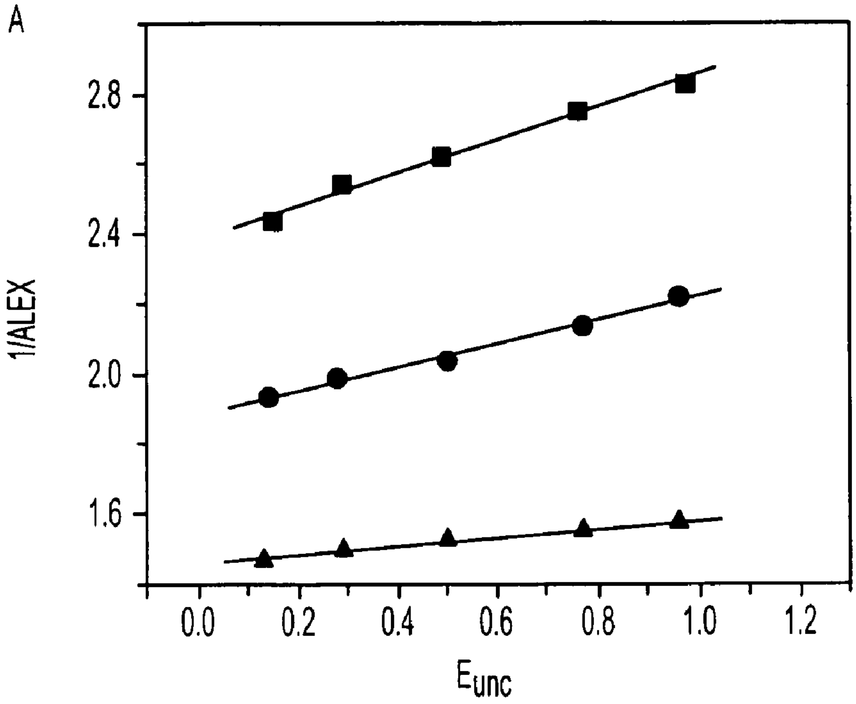
FIG. 7A shows an exemplary histogram based on alternating-laser-based ratios 1/ALEX and $E_{unc}$ for 5 DNA fragments that contain two fluorophores that are spaced by increasing distances and participated in FRET to a different extent. The fit of the 5 points to a straight line allow extraction of the detection correction factor γ that allows the measured of accurate FRET efficiencies at the single-molecule level. The plot also recovers excitation-dependent parameter β.
FIG. 7B is a plot of β and γ at different excitation-intensity ratios, showing that γ is independent of the ratio of excitation intensities used for alternating-laser excitation experiments.
Figure 7:
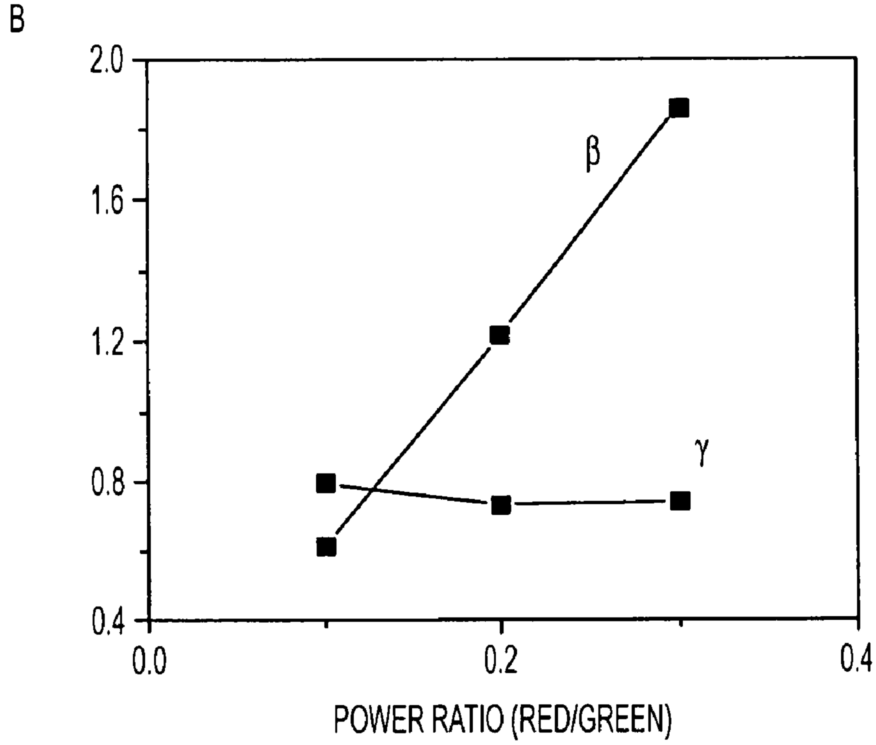

By measuring 1/ALEX and $E_{unc}$ of samples featuring different E values, but having donor and acceptor fluorophores with identical optical properties (such as quantum yield, extinction coefficient, absorbance and emission wavelength), one can obtain the value of 1+βγ (intercept) and −β(γ−1) (slope), which extract the emission correction factor γ. FIG. 7A shows such a case for DNA fragments featuring donor and acceptor fluorophores separated by 8, 13, 18, 23, and 28 bp DNA (Donor: TAMRA, Acceptor: Alexa 647), under three different excitation-intensity ratios (donor-excitation/acceptor-excitation ratios of 100: 30, 100:20, and 100:10). Each excitation-intensity ratio gave a linear plot, and yielded constant values for γ (γ~0.73), and power-dependent values for β (FIG. 7B). The determination of the excitation correction factor β bypasses the need for "balancing" the emissions, which was necessary for the limiting case (Eq. 5) of ALEX-FRET. Inserting this a into equation (9), one can obtain an E value corrected for instrumental factors. It is noteworthy that $E_{instr\text{-}corr}$ does not depend on alignment of the detection hardware, whereas uncorrected E values are alignment-dependent. Thereby, this example demonstrates that the method of the present invention is capable of obtaining γ experimentally, yielding accurate E values. Methods for obtaining correction factors from ALEX-FRET on a single sample are highly desirable (since they bypass the need from preparation, measurement and analysis of multiple samples acting as standards). One way to implement such methods is by changing red laser excitation intensity.

EXAMPLE 5

Analysis of Protein -DNA Interactions

The present invention may be used to analyze the interaction of nucleic-acid—binding proteins with nucleic acids. Such proteins can be DNA- or RNA-binding proteins, transcription or translation factors, and DNA-or RNA processing enzymes (such as DNA-repair machinery, DNA or RNA polymerases, DNA integrases, and DNA topoisomerases), and can serve as excellent targets for drug development [41, 42]. At the same time, the methods of the present invention can be used to advance mechanistic understanding of nucleic-acid related bioprocesses that malfunction during human disease, which is necessary for rational drug design.

In this example ALEX-FRET in accordance with the present invention was used to demonstrate specific protein-DNA interactions, and to extract equilibrium binding constants for two systems: i) the interaction of a transcription factor (*Escheirichia coli* catabolite activator protein, CAP) with DNA, and ii) the interaction of a DNA-processing enzyme (*E. coli* RNA polymerase) with DNA.

This was performed by preparing small-volume (5-50 μl) samples containing 50-100 pM acceptor-labeled DNA and increasing concentrations (0-500 pM) of donor-labeled protein, performing ALEX-FRET in the same manner as Example 1, identifying individual acceptor-containing species by burst analysis, and calculating the extent of binding as the binding ratio: [donor-acceptor species]/{[donor-acceptor species]+[acceptor-only species]}. In the absence of donor-labeled protein, all DNA appears as an acceptor-only species, and there is no binding. Increasing concentrations of the protein leads to formation of complexes that appear as donor-acceptor species in ALEX-FRET. These correspond to increased binding ratios. Upon saturation of the DNA, all acceptor-only species are converted to donor-acceptor species and the binding ratio is approximately 1.

Figure 8:
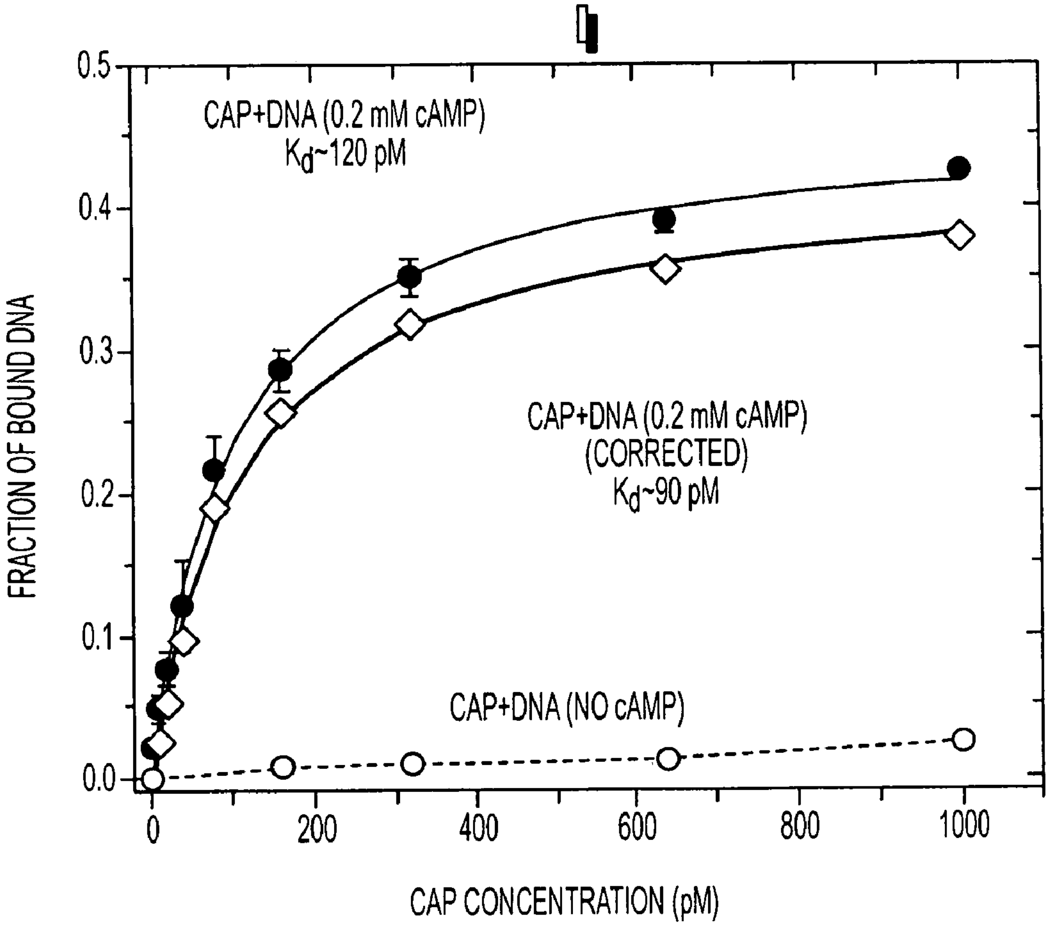
FIG. 8 is a graph depicting the results of an analysis of DNA binding to CAP which was carried out using the method of the present invention.

The concentration-dependence of the binding ratio resembles a rectangular hyperbola. Upon simple non-linear fitting, the equilibrium binding constant can be extracted. An example of such a titration is shown in FIG. 8 which shows the specific binding of transcription factor CAP (catabolite activator protein) to a DNA fragment that contains a specific DNA sequence. This binding has a dissociation constant of approximately 100 pM, consistent with values obtained in the literature using ensemble methods. The binding of CAP to DNA is only observed in the presence of cyclic AMP, which converts the protein to an active conformation. Absence of cAMP results in absence of CAP binding to. DNA, and serves as an excellent control for the evaluation of the part of the signal that is due to the random coincidence of D- and A-labeled molecules. At the concentration range used, the random coincidence background is very small, and its subtraction does not change the recovered affinity significantly. Details of this example are provided in U.S. Provisional Application Ser. No. 60/572,559.

The ability to monitor protein-DNA FRET as well as coincidence of protein and DNA increases the information content of the analysis. For example, if there are two possible interaction sites on DNA (eg. one high-affinity specific site and a second, low-affinity non-specific site), it is possible to distinguish between them by the different FRET values that are generated upon complex formation. This way, two binding constants (corresponding to the two distinct protein-DNA complexes) can be extracted from the same sample (something not possible using FFS methods).

The present invention analysis works well when the acceptor-only and donor-acceptor species do not have significantly different diffusion times (difference in diffusion time approximately 10%). This can be achieved either by using long DNA fragments (100-150 base-pairs in length) that do not change diffusion time significantly upon complexation with protein, or by using short DNA fragments and reverse the order of the titration (have a constant concentration of protein and titrate with increased concentrations of DNA.

If the two species have significantly different diffusion times (e.g. donor-acceptor protein-DNA species has diffusion times 2-fold higher the acceptor-only DNA species), then there is a higher probability to detect the slower-diffusing species. To account for such a bias in our example, the number of acceptor-only DNA species in the absence of donor-labeled protein can be compared to the number of donor-acceptor species upon saturation of DNA (essentially in the absence of acceptor-only DNA species). This way, the correction factor can be considered in the non-linear fitting routine, and any diffusion-time (or otherwise induced) skeweness in the calculation of equilibrium binding constants can be removed. It is important to note that in many cases, such a correction might not be necessary. For example, in the case where the disruption of an interaction as a function of the identity of a chemical member of a compound library occurs, a more rigorous and general correction can involve extraction of diffusion-times and molecular brightness values from ALEX-FRET combined with burst analysis.

Analysis of Protein-Protein Interactions

Considerations similar to protein-DNA interactions apply to the detection and quantitation of protein-protein interactions. In this case, the two proteins to be tested for interactions are labeled ‘green’ and ‘red’ respectively, and protein-protein interactions with dissociation constants within the concentration range of ALEX-FRET are studied by titrations of a constant amount of the larger protein with increasing amounts of the smaller protein (to minimize any diffusion-time bias in the recovered species). Advances that extend the range of accessible concentrations and facilitate site-specific protein labeling will be instrumental for extending the application of ALEX to protein-protein interactions of any affinity.

Protein-DNA Titrations Based on Protein-Dependent Association of DNA

A specific application of the present invention allows quantitation of the affinities of homodimeric transcription factors for their binding sites (and their permutations) and allows quantitation of transcription factor in complex samples such as nuclear extracts. This is accomplished by extension of a published ensemble-fluorescence method termed “molecular beacons for DNA-binding proteins” [43-45]. The central feature of the ensemble assay is the protein-dependent association of two DNA fragments each containing a half-site responsible for protein-binding. The extension of the DNA beacon to ALEX-FRET bypasses two important limitations of ALEX-FRET: the need for protein labeling; and the limited concentration range for monitoring interactions. Beacon-based ALEX-FRET allows monitoring of protein-DNA interactions without the need for protein labeling. Since the protein component is not labeled, any concentration of protein components in the assay can be used. This allows measurement of dissociation constants much higher than the concentration limit imposed by the requirement for detecting individual fluorescent species. The method of the present invention is fully compatible with the ensemble DNA beacon assay, offering two distinct advantages. First, the present invention removes the proximity-constraint (due to requirement of FRET) necessary for the ensemble assay. This allows incorporation of the fluorophores at any point along the half-site DNA fragments used as beacons, removing potential perturbations of the protein-DNA interaction by the fluorophores used. Second, the present invention allows probing of the interactions using 1000-fold lower concentrations of the DNA beacons and in volumes 100-fold smaller than the ensemble-FRET assay. This results in significant savings of reagents, allowing use in high-throughput screening formats.

The concept of interaction-dependent coincidence detection of two fluorescent molecules with distinct emission can be extended to identification and quantitation of biomolecules other than DNA-binding proteins. For example, hybridization of short DNA fragments (each carrying a fluorophore with distinct emission) that are complementary to a specific RNA molecule can be detected as an intermediate-ALEX, low-E species in the E-ALEX histogram. If no RNA is present, no RNA-DNA hybridization will occur, and therefore only free DNA fragments (equivalent to donor-only and acceptor-only species in the E-ALEX histogram). This allows for the identification and quantitation of specific messenger RNA (that might code, for example, for disease-related proteins) produced in different cells or at different points of the cell growth and development. The identification of an array of specific RNA molecules (that can be probed with different pairs of fluorescent DNA fragments) in cellular extracts will provide rapidly a comprehensive picture of the expression patterns and the physiology of cells without the laborious and time-consuming processes of complementary DNA (cDNA) synthesis, PCR amplification, and DNA-chip hybridization arrays that are currently used to monitor gene expression. Similar procedures can provide quantitation of specific proteins or multi-protein complexes.

Measurement of Off-Rates for Bimolecular Complexes

Figure 9:
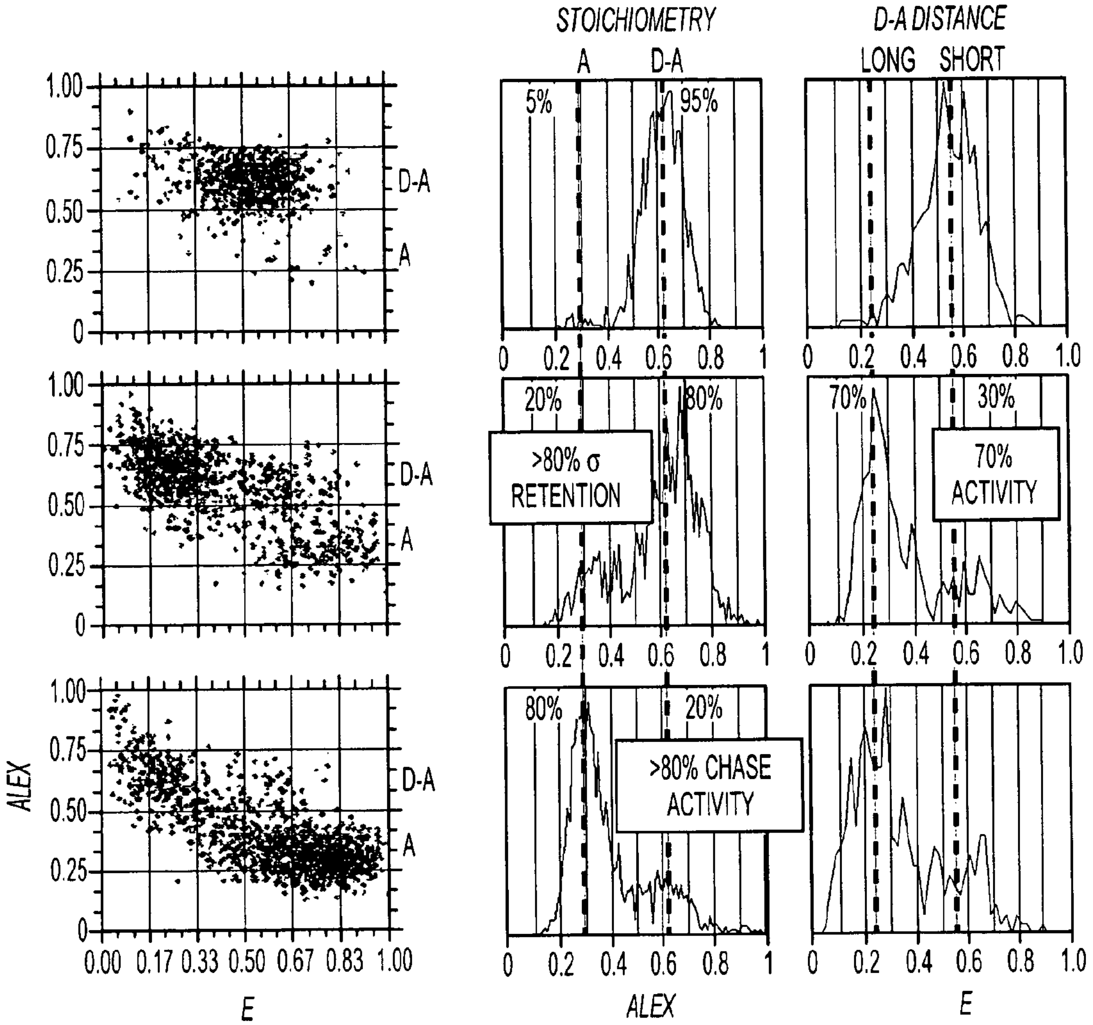
FIG. 9 depicts the results obtained using the method of the present invention to analyze bimolecular interaction between RNAP and DNA.

The affinity of an interaction can be evaluated by measuring the off-rate of bimolecular (AB) complexes by observing the kinetics of dissociation of donor-acceptor species (with or without FRET). The affinity of an interaction is proportional to the association constant $K_a$ and inversely proportional to the dissociation constant $K_d$($K_a$=1/$K_d$). Since $K_a$=$k_{on}$/$k_{off}$ (where $k_{on}$ and $k_{off}$ are the on- and off-rates, respectively), and since the on-rates usually do not vary significantly from the diffusion-limited rates (approximately $10^9$ $M^{-1}$ $sec^{-1}$), the off-rates are the main determinants of the affinity of an interaction; slow off-rates correspond to a high affinity interaction. Determination of the off-rates can be performed by forming potential AB complex at high concentrations (greater than 10-1000 nM), diluting the complex at SMFS-compatible concentrations (50-100 pM) and monitoring the kinetics of loss of donor-acceptor coincidence signal. The rate constant is the off-rate for the interaction. This will allow extraction of information about weakly-bound complexes (where dilution disrupt complexes immediately, resulting exclusively in donor-only and acceptor-only species), strongly-bound complexes (where dilution results in donor-acceptor species that do not dissociate significantly after hours of observation) and cases that fall between the two extremes. An example of determination of off-rate is shown for a protein-DNA complex (the CAP-DNA complex) (FIG. 9). The off-rates were determined in two different buffers, showing two different rates of dissociation, with use of potassium glutamate-based-buffer resulting in a complex that dissociates more slowly than the case of use of sodium-chloride-based buffer.

Structural Analysis of Complex, Multi-Component Mixtures

Figure 10:
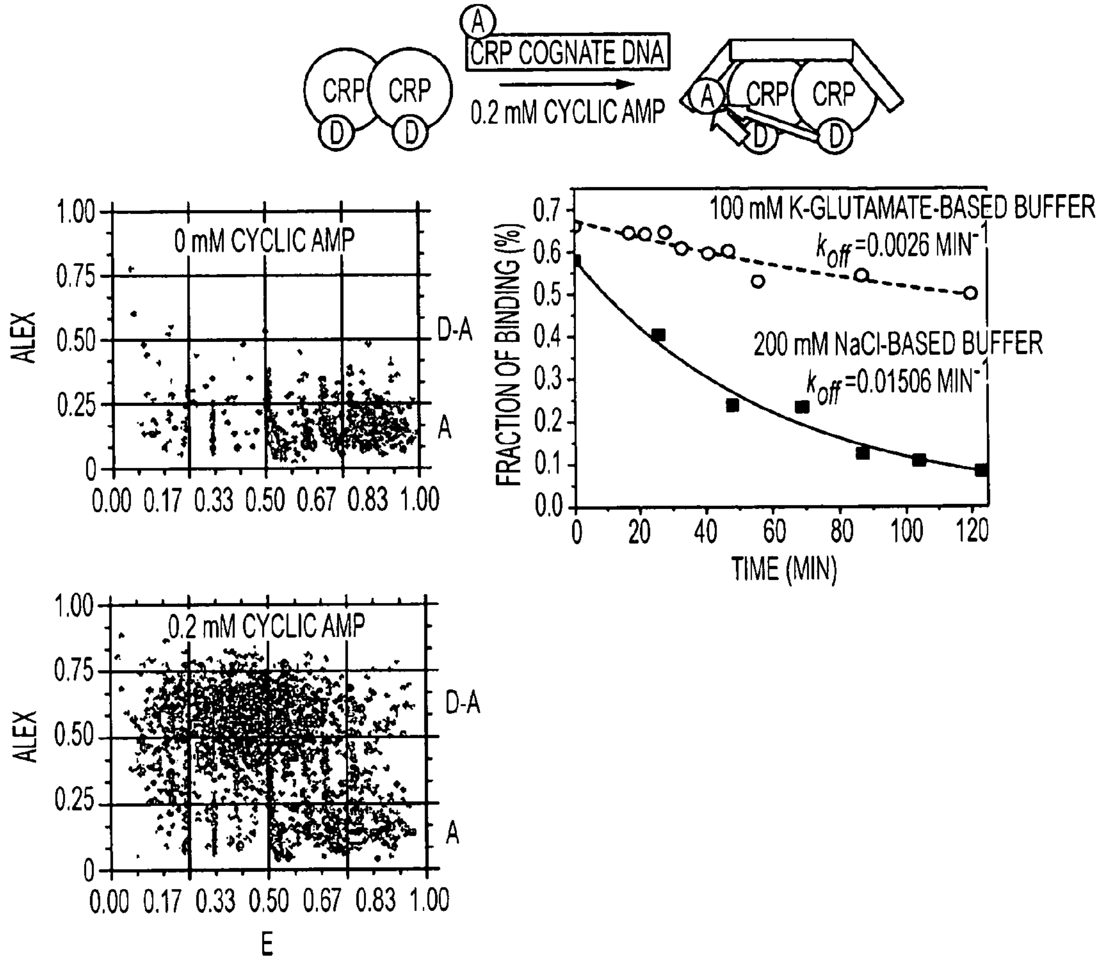
FIG. 10 depicts the results obtained using the method of the present invention to determine off-rates for a bimolecular complex (CAP-DNA).

The ability to extract stoichiometry and distance information simultaneously allows deconvolution of the heterogeneity present during the formation of large, multi-component complexes. This allows the initial identification of heterogeneity that is difficult or impossible to observe by ensemble or FFS methods, as well as the characterization of the various species. Some of the rare, difficult-to-observe biological intermediates might have great implications for development of pathological conditions. In this example, we demonstrate the ability of the present invention to perform structural and functional analysis of complex mixtures by analyzing the formation of initial transcription and transcription elongation RNAP-DNA complexes. For initial transcription complexes (FIG. 10) we identified the presence of a structurally-homogeneous RNAP-DNA complex (as an intermediate-ALEX, high-E species); addition of reagents for the formation of elongation complex resulted in the identification of an active population of the initial complex (approximately 80%) that result in translocation of RNAP on DNA, and an inactive population (approximately 20%). Details of this example are provided in U.S. Provisional Application Ser. No. 60/480,346. Apart from demonstrating the general character of the analysis (can be applied on any protein-protein or protein-DNA complex), assays using bacterial transcription systems are important for the development of new antibacterial agents (such as antibiotics) that act at the levels of transcription initiation and elongation.

Determination of Macromolecular Structure

Methods in accordance with the present invention can also be used to generate distance-based constraints that will allow determination of macromolecular structure in solution. This can be performed by sub-stoichiometric, statistical labeling of macromolecules (proteins or nucleic acids) with donor and acceptor fluorophores that can be incorporated using orthogonal chemical reactions (e.g. the donors are incorporated using reactions with amine groups, whereas acceptors are incorporated using reactions with sulphydryl groups). At low concentrations, the mixtures of molecules with various labeling stoichiometries can be sorted using ALEX and bright species with 1:1 (donor:acceptor) stoichiometry can be identified and analyzed in terms of distance, as well as donor and acceptor environment.

After selection of subpopulations in the ALEX histogram, subpopulations can be analyzed by many data analysis methods. For example, auto- and cross-correlation analysis can be used to determine diffusion (molecular mass), photophysics, conformational dynamics and the like. If time-correlated single photon counting is performed, the lifetime histograms for individual subpopulations can be extracted, allowing for analysis of multiple exponentials (indicative of distance distributions and fluorescence anisotropy). By performing analysis on specific subpopulations, important characteristics can be extracted. Bulk measurements obtain information about the ensemble, single-molecule measurements provide information about individual members of the ensemble, and subpopulation measurements provide information on specific species.

The method of the present invention can be combined with an FFS method, such as PAID (W02004/011903A2), to provide extraction of more parameters about the species present in complex mixtures and permit operation at higher concentration of fluorescent analyte, without the cost and complexity associated with SMFS measurement using pulse-laser excitation and time-correlated single-photon-counting acquisition. PAID can be used to analyze ALEX results generated using an alternation period of 10 μs. The PAID model is still valid for such a period, which is still slower than the modulator response time and will still provide information. Otherwise, a slightly-modified PAID model will be necessary. This will allow increase in the range of working concentrations of ALEX without the complex and relatively expensive instrumentation (excitation sources, TCSPC detection equipment) required for nsALEX.

Methods for determination of diffusion times of single molecules based on burst-duration distribution analysis [46], and for the determination of molecular brightness based on burst size distribution analysis have been described [37]. Improved modeling of the diffusion process provided by the present invention will allow burst-based extraction of diffusion times and molecular brightness for distinct species. This will further improve the resolution capability of the present method and account for differences in the analysis that arise due to the different diffusion-time of the resolved species.

Evanescent-Wave-Based ALEX

Using evanescent-wave excitation and the wide-field area detection of a CCD camera (time-correlated single photon counting imager), it is possible to perform extended observations of greater than 100 individual immobilized molecules at the same time. Using objective-based Total-Internal-Reflection (TIR) microscopy (or wide-field illumination) and two different laser-excitation paths, one can focus the excitation individually at the back focal plane of a high numerical-aperture (1.45) objective and generate an evanescent field for each of the two excitation wavelengths. Alternate-laser excitation is achieved using two software-controlled shutters, triggered by the CCD camera, resulting in 100-ms excitation pulses corresponding to 100-ms frames on the CCD camera. The present method is also applicable to prism-type TIR. Detection is achieved in a double-view mode, allowing for the simultaneous recording of the donor-emission and acceptor-emission channels. Image analysis is performed using the same procedures as single-laser-excitation TIR-FRET, except that for each single molecule a trace of A-excitation-dependent A-emission signal ($F^{aA}$) is generated in addition to the donor-excitation-dependent donor-emission ($F^{dD}$) and donor-excitation-dependent acceptor-emission ($F^{dA}$) traces. This additional information allows one to identify acceptor-only species and to distinguish between low-FRET donor-acceptor species and donor-only species with the results being summarized in E-ALEX histograms. Evanescent-wave-based ALEX combined with a scanning x-y stage can be useful for assays performed using DNA- and protein-arrays, by using assay principles described above for diffusing species.

Similarly, the present invention can be applied to a single immobilized molecule to record time-trajectories of ALEX and FRET. This allows for corrections of FRET due to changes in the photophysics of the acceptor. Confocal scanning of the surface can also be used to generate donor-excitation-dependent images and an acceptor-excitation-dependent images. Using the same expression described above for diffusing molecules, one can identify donor-only, acceptor-only and donor-acceptor molecules and identify the E value of the donor-acceptor species.

EXAMPLE 6

Nanosecond ALEX and ALEX-PAID

The Nanosecond Time Domain

Figure 11:
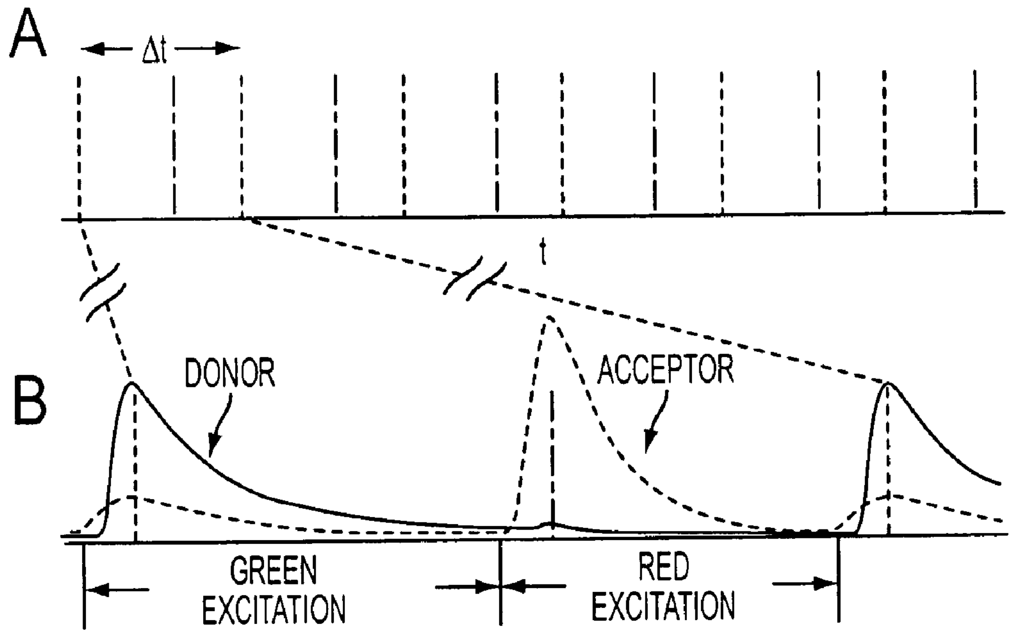
FIGS. 11A and 11B depict the interlacing of two pulsed lasers to obtain alternating periods in the nanosecond time domain.

A limitation of FFS methods is the potential presence of fluorophore interactions (such as FRET). Combinations of ALEX with an FFS method (such as PAID) are desirable since they extend the working range of concentrations. However, laser alternation on the 20-100 μs time scale precludes PAID, since the PAID model is no longer valid, and the alternation masks temporal dynamics on that time scale. In order to combine ALEX with PAID, the alternation period must become much shorter. This is possible by interlacing the pulses from two synchronized pulsed lasers, one exciting the ‘green’ (donor) fluorophore, the other exciting the ‘red’ (acceptor) fluorophore (FIG. 11A and B). The pulse repetition rates are typically 50-100 MHz, thus decreasing the alternation period for ALEX by a factor of greater than 1000. By using time-correlated single-photon counting, photons correlated with the first excitation pulse can be separated from photons correlated with the second excitation pulse. FRET-dependent acceptor emission can be clearly separated from emission caused by direct excitation to thereby allow the ALEX analysis to be performed without changes. Moreover, PAID analysis with three effective channels (donor, acceptor sensitized emission, and acceptor direct excitation) can be performed at higher concentrations than with the single-molecule burst analysis to simultaneously extract more information. By combining ALEX with PAID, one can detect macromolecular interactions regardless of the distance between fluorophores, up to approximately 10 nM concentrations.

Figure 12:
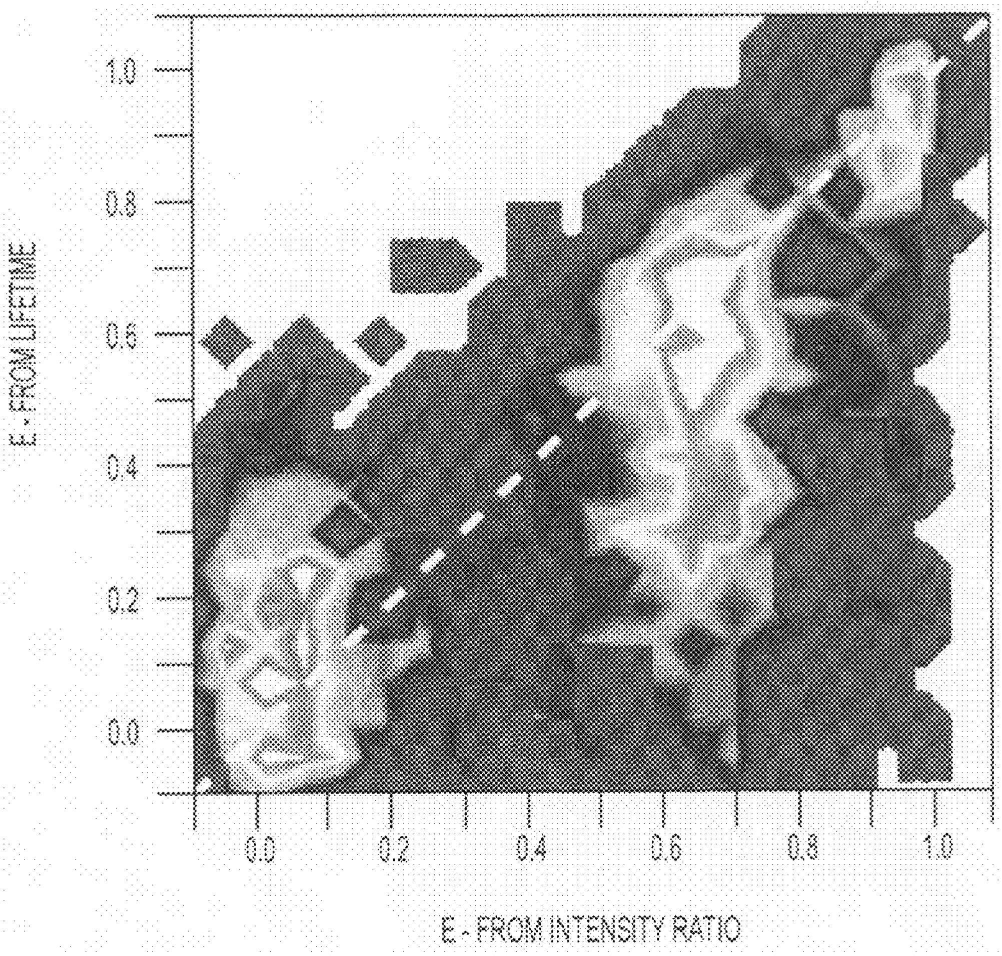
FIG. 12 is a two-dimensional histogram of energy transfer efficiency E that is measured for photon bursts detected from single molecules of the protein C12 in 4M GuHCl (near the midpoint of the denaturation curve). Three species are present in the histogram: the folded molecules are on the upper right, the unfolded molecules are in the middle and the molecules with photo-bleached Cy5 are on the lower left. The factor γ was set to 1.2.
Figure 13:
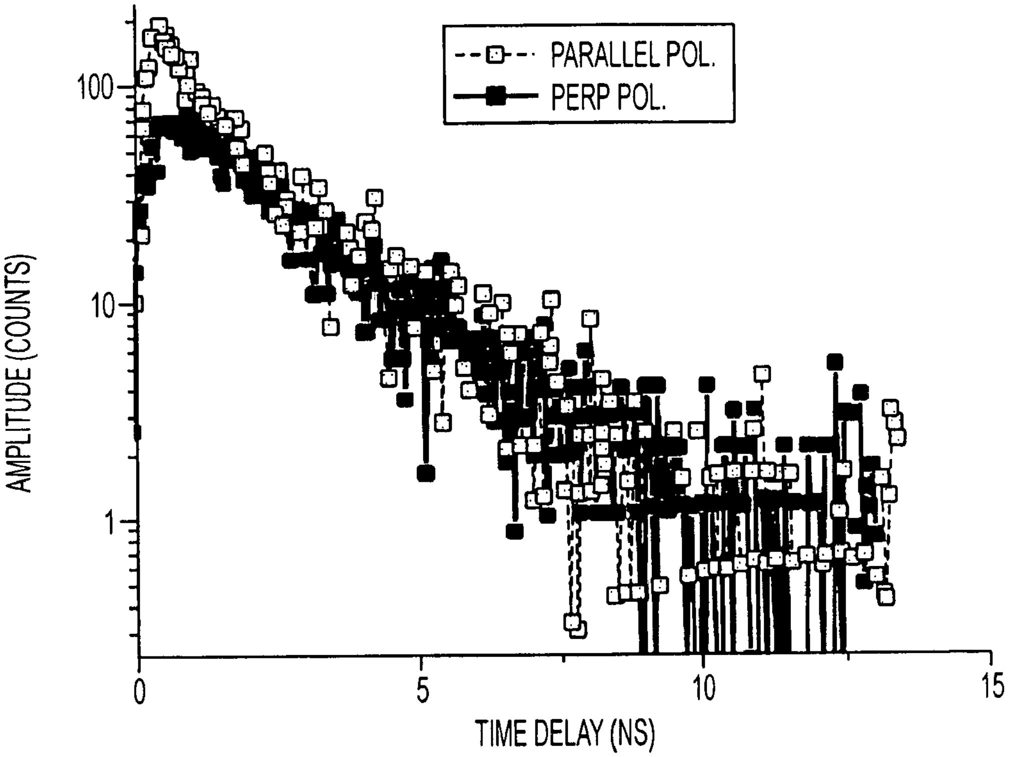
FIG. 13 is a graphic comparison of the TMR fluorescence-intensity decay curve for the detection channels with polarizations parallel and perpendicular to the excitation polarization, summed over the unfolded subpopulation. This histogram shows that there is a component due to rotational diffusion of TMR (multiple exponentials due to distance changes would be the same for both polarizations).

Additional Information Obtained Using ns-ALEX: Fluorescence Lifetime & Anisotropy Since the data can be acquired using time-correlated single-photon counting, the fluorescence lifetime of the donor and acceptor fluorophores can be extracted, providing another observable for measuring FRET efficiency, and resolving subpopulations (FIG. 12). Moreover, the addition of polarizing beamsplitter cubes in the detection paths of the donor and of the acceptor after the spectral separation of the two wavelength ranges allows the measurement of time-related fluorescence anisotropy for every diffusing molecule (FIG. 13). There are several benefits to ns-ALEX in combination with polarization information:

1) The simultaneous determination of FRET by lifetime ($E=\tau_D^A/\tau_D$, where $\tau_D^A$ and $\tau_D$ are the fluorescence lifetime of the donor in the presence and absence of the acceptor, respectively) and intensity lowers biases and improves confidence in the conclusions. This is because FRET determined by lifetime has lower bias, since the relative quantum efficiency of donor and acceptor and the relative detection efficiencies of the detector channels do not play a role.
2) Several type of fluorescence anisotropy ($r=I_{\Box}-I_{\perp}/I_{\Box}+2I_{\perp}$) may be determined, sometimes assisting in separating subpopulations. More importantly, this helps to determine accurate distances from FRET efficiency. Two anisotropies, $r_D$ (anisotropy of donor in presence of acceptor) and $r_{DA}$ (anisotropy of acceptor emission caused by FRET from donor) are determined from laser excitation d. Another anisotropy, $r_A$ (anisotropy of acceptor when excited directly), is determined from laser excitation a. All three anisotropies are required to obtain the best estimates on the error of distance.
3) The anisotropy decay caused by rotational diffusion can be monitored simultaneously with the other observables. This provides information on the local and global mobility of the fluorophores.
4) Distance distributions that fluctuate faster than the diffusion-crossing of the species (but slower than fluorescence lifetime) can be probed with ns-ALEX, since these distributions will result in multi-exponential lifetime distributions.
5) Interactions/binding constants can be derived both from the present invention and from single molecule polarization anisotropy data. The extra information can yield better subpopulation resolution and more accurate constants.

Nanosecond ALEX (ns-ALEX) in accordance with the present invention is based on modulation (alternation in the case of modulation between two wavelengths, intensities and/or polarizations) periods that are in the range of approximately 1 or less nanosecond to a few microseconds. ALEX with modulation periods on the order of a few microseconds are referred to as μs-ALEX. The faster time scale of ns-ALEX allows one to extend ALEX to provide information on three more observables: fluorescence lifetime, time-resolved fluorescence anisotropy and enhanced dual-color cross-correlation.

Interlacing pulses from two mode-locked lasers provides the additional benefit of a much faster alternation (modulation) period (approximately 15 nanoseconds). This allows one to extend ALEX data acquisition further to include information on fluorescence lifetime by using time-correlated single-photon counting (TCSPC).

In addition, one can simultaneously monitor the polarization of emitted photons by splitting the signals detected singly in ALEX into two different polarizations, to obtain time-resolved fluorescence anisotropy, which is important for the conversion of FRET efficiency values to real distance estimates, and for correctly fitting the fluorescence lifetime decays. This is important for analysis of distance fluctuation and distribution within single molecules. Time-resolved fluorescence anisotropy also provides additional information on molecular interaction by monitoring rotational diffusion that reports on molecular mass changes.

With this time stamping, one can also simultaneously sort photons according to their arrival times and perform a more accurate dual-color cross correlation analysis by preventing “cross-talk” from donor emission into the acceptor channel, “corrupting” the data. By alternating laser excitations with precise timing and categorizing photon streams according to their excitation source, we can exclude the fluorescence leakages from extended fluorophore spectra and perform dual-color fluorescence correlation spectroscopy (FCS) on a doubly-labeled molecule or bound species of two different singly-labeled molecules, greatly improving FCS studies. By doing the leakage-excluded cross-correlation analysis, one is able to recover the non-correlating feature between two singly-labeled molecules which conventional cross-correlation fails to show due to leakage effects. By carefully applying fitting routines for the two-color cross-correlation curves, we are able to extract accurate occupancies for different species (bound/free) inside the excitation volume (at higher, approximately nM concentrations) and thus probe weaker binding affinities between molecules in the sample.

Ns-ALEX is preferred over μs-ALEX for some applications. For example one obtains a more complete characterization of macromolecular interactions, such as fluorophore stoichiometry, internal distance distributions of specific species (molecules), fast conformational dynamics of macromolecules, rotational diffusion-related effects, in addition to a wider dynamic range. Also, the addition of FCS allows quantification of labeled molecules on a higher-than-single molecule concentration level, thus enabling one to measure a broad range of concentrations with the same data acquisition method, assuming a homogenous population.

Now, with a single methodology, one can analyze a wide range of protein-protein interactions and quantify expression levels. The only requirements for this embodiment of the present invention is that interacting species be fluorescently labeled with the exact stochiometry of one dye label per one protein or one DNA molecules. DNA labeling techniques are well characterized [51] and may be used to provide site-specific and stoichiometric fluorescent labeling of proteins and/or DNA molecules.

A general approach for the site-specific labeling of proteins from a cell has not been available; however, several techniques have been developed recently to site-specifically label recombinant proteins. There are two promising methods for site-specific labeling of recombinant proteins from MR-1. The first utilizes a specific recombinant tag that expresses a tetra-cysteine motif, C—C—X—X—C—C (where X is any amino acid except cysteine) at the protein termini [52]. This tag reacts with a fluorescein or resorufin dye conjugate with two arsenic groups, FlAsH or ReAsH respectively. The arsenic groups readily react with pairs of thiols, and the motif spacing enables dye binding with site-specificity and high affinity (<10 pM $K_d$), in vitro and in vivo. The second approach relies on the modification of the amino terminus of the protein with a cysteine residue and the additional modification of succimidyl ester dyes to thioesters [53] This technique, similar to peptide ligation, requires a constructed expression vector for the terminal modification through protease activity, and once the desired amino terminal cysteine is achieved labeling proceeds directly and site specifically through a two step irreversible reaction that is limited to in vitro applications.

Both techniques have advantages and disadvantages associated with dye synthesis and vector construction, yet both techniques offer unique universal labeling strategies without extensive sequence mutations associated with conventional amine or cysteine labeling. These techniques can be incorporated with the present invention to achieve a universal site-specific labeling of recombinant proteins, such as recombinant MR-1 proteins and a universal scheme for any recombinant protein from any microbe.

Mapping Macromolecular Interactions with μs-ALEX-FAMS

Making the leap from an optical method to a global-scale tool for the elucidation of complex dynamic circuitry nodes requires a scalable methodology capable of analyzing a variety of macromolecular interactions. Since μs-ALEX can be used to simultaneously report on association status and conformational status, it is suitable for the analysis of macromolecular interactions. To demonstrate the capabilities of μs-ALEX, we examined its abilities to distinguish differing D-A stoichiometries, modeling protein oligomerization, and analyze macromolecule-ligand interactions on a model system of protein-DNA, modeling protein-protein interactions.

Protein oligomerization is a common modulator of protein function, and since S, the stoichiometry ratio, is sensitive to the ratio of donors/acceptors per molecule (e.g. for species $D_2$-A, D-A, and D-$A_2$, S($D_2$-A)>S(D-A)>S(D-$A_2$)), it can be used to monitor protein oligomerization. To demonstrate this, we compared DNA carrying one donor and one acceptor with DNA carrying two donors and one acceptor. The E-S histograms for the two DNA fragments were distinct (mainly along S). As expected, S($D_2$-A) was greater than S(D-A). Analysis of a 1:1 mixture of $D_2$-A and D-A yielded an E-S histogram having a single D-A peak with a wide S distribution. This is consistent with two species with closely spaced S distributions. Using a constrained double Gaussian fit (with individual distributions described using means and standard deviations of pure $D_2$-A and D-A), we recovered a D-A: $D_2$-A ratio of 0.9:1. Hence, μs-ALEX of the monomeric and dimeric forms of a dimerizing system permits extraction of the ratio of D-A and $D_2$-A species as a function of the concentration of D-labeled molecule. As a result, one can use μs-ALEX to examine oligomerization and determine dimerization constants.

To illustrate the above features of the present invention, we studied the sequence-specific interaction of *E. coli* catabolite activator protein (CAP) with DNA. We monitored the interaction of D-labeled CAP (as the "ligand" $CAP^D$) with its consensus A-labeled DNA site (as the "macromolecule" $DNA^A$), with or without the allosteric effector cyclic AMP (cAMP). With 0.2 mM cAMP, $CAP^D$-$DNA^A$ complexes were detected as D-A species. $CAP^D$-$DNA^A$ complexes appeared as a wide and heterogeneous E distribution. High E values were consistent with a 60-100° overall DNA bend towards CAP. Without cAMP, few complexes were formed. These rare species had E values similar to the ones seen in the presence of cAMP. To assess equilibrium binding for the CAP-DNA interaction, we titrated 10 pM $DNA^A$ with 0-300 pM active $CAP^D$, identified A-containing species, and calculated θ for each [$CAP^D$]. With cAMP, the dependence of θ to [$CAP^D$] resembles a rectangular hyperbola ([D-only]=[$CAP^D$]). Upon fitting, $K_d$ was 32±3 pM, which was in good agreement with filter-binding-based values (24±2 pM [43]). Without cAMP, CAP binds to DNA >150-fold weaker ($K_d$>5 nM).

We also monitored dissociation kinetics of $CAP^D$-$DNA^A$ by forming the complex, diluting it in 50-fold molar excess unlabeled CAP (to sequester $DNA^A$ formed due to dissociation) and observing the kinetics of θ decrease. When θ decrease is fitted as single exponential decay the $k^d$~(1.1±0.2) $*10^{-4}$ $s^{-1}$ is in agreement with gel-based-assay values. ALEX can also be used to monitor association kinetics, by fast mixing of low concentrations of CAP and DNA, and monitoring of the kinetics of θ increase.

Quantifying mRNA Expression Level With ns-ALEX

The robust nature of the μs-ALEX and ns-ALEX methods in accordance with the present invention allows one to quantify levels of gene expression by directly quantifying mRNA utilizing the same principles as the previously described exemplary interaction analysis. By designing synthetic fluorescently labeled oligonucleotide probes to the mRNA of interest, one can detect D-only, A-only, and D-A species using the ns- and/or μs-ALEX method. Through photon-counting or cross correlation spectroscopy one can quantify the subpopulations to determine the concentration of target molecule in the sample. To demonstrate this ability, we initially designed a synthetic DNA system to model mRNA detection.

We monitored the hybridization of a D-labeled probe and an acceptor labeled probe to an unlabeled target DNA molecule. Hybridization was monitored by titrating an increasing concentration of probes against a constant concentration of target. Cross correlation was used to calculate the concentration of bound species at each point and a titration curve was constructed to calculate target concentration in the solution. By applying this method to a series of different target concentrations, one can generate a calibration curve for measuring unknown saturated target concentration. With the target concentration successfully determined, one can easily apply this methodology on any mRNA system.

Evaluation of FlAsH ReAsH Dyes for Universal Labeling Schemes

A protein conjugated with FlAsH and ReAsH dyes was photophysically characterized using the method of the present invention. A calmodulin protein was expressed with a recombinant tetra-cysteine motif, C—C—X—X—C—C (where X is any amino acid except cysteine) at the protein termini and conjugated with either FlAsH or ReAsH. We examined the photophysical stability of these dyes attached to the protein with fluorescence correlation spectroscopy to examine their potential use in SMFS.

From our preliminary studies using ALEX in accordance with the present invention, the FlAsH dye is stable with increasing laser excitation, and the time traces reveal bursts comparable with other single dyes. Analysis of FCS curves taken with powers ranging from 200 μW to 2.5 mW reveals moderate changes in diffusion and photobleaching with increasing laser power, but no significant bleaching at powers relevant for single molecule studies. The ReAsH dye was assessed with a far from efficient excitation wavelength at (green HeNe laser 543 nm); nevertheless, even with this less than optimal excitation, the dye still emitted single molecule bursts appropriate for use in ALEX. With a 594 nm laser, the ReAsH dye is expected to show the same level of stability as FlAsH. These preliminary studies suggest that the FlAsH and ReAsH dyes will work- well for single molecule analysis.

Using DNA and protein-DNA model systems, we have only demonstrated exemplary applications of ns- and μs-ALEX. The present invention can be used to characterize pair-wise protein-protein interactions, calculate biomolecular constants ($K_d$, $K_{on/off}$), determine stoichiometry of multi-protein complexes, either homo- or hetero-oligomeric and examine conformational dynamics through FRET. The in-depth analysis of protein-protein interactions moves beyond protein chips and mass spectroscopy methods to provide quantitative information about interacting partners molecules and their strength of interaction. Additionally, the dynamic range of ns-ALEX-FAMS and lack of washing or mixing steps allows weak binding molecular partners to be analyzed, providing new information on transient protein-protein interactions. With this quantitative information, complex regulatory circuits can be reconstructed with some a priori knowledge of the proteins involved. Also, proteins of unknown function can be screened for interactions with protein of known function to provide characterization through 'guilt by association'. Moreover, this quantitative expansion is not limited to protein-protein interactions. The same analysis that provides quantitative information about protein interactions can be utilized to determine expression levels.

The analysis may takes place in two modes, a burst analysis mode and a modified fluorescence correlation mode. The first mode is applied to low concentration samples where single molecules are detected; at these concentrations (100 pM to 1 nM), less than one molecule resides in the detection volume [54]. In this regime detected photon bursts correspond to single molecules diffusing through the confocal spot. With ALEX, these bursts are detected and plotted on 2-D histograms correspond to donor only, acceptor only, and bound species. These subpopulations correspond to free interactants and complexes in solution, and equilibrium binding and kinetic rate constants can be directly measured by simply counting molecules of the 3 major species.

Figure 15:
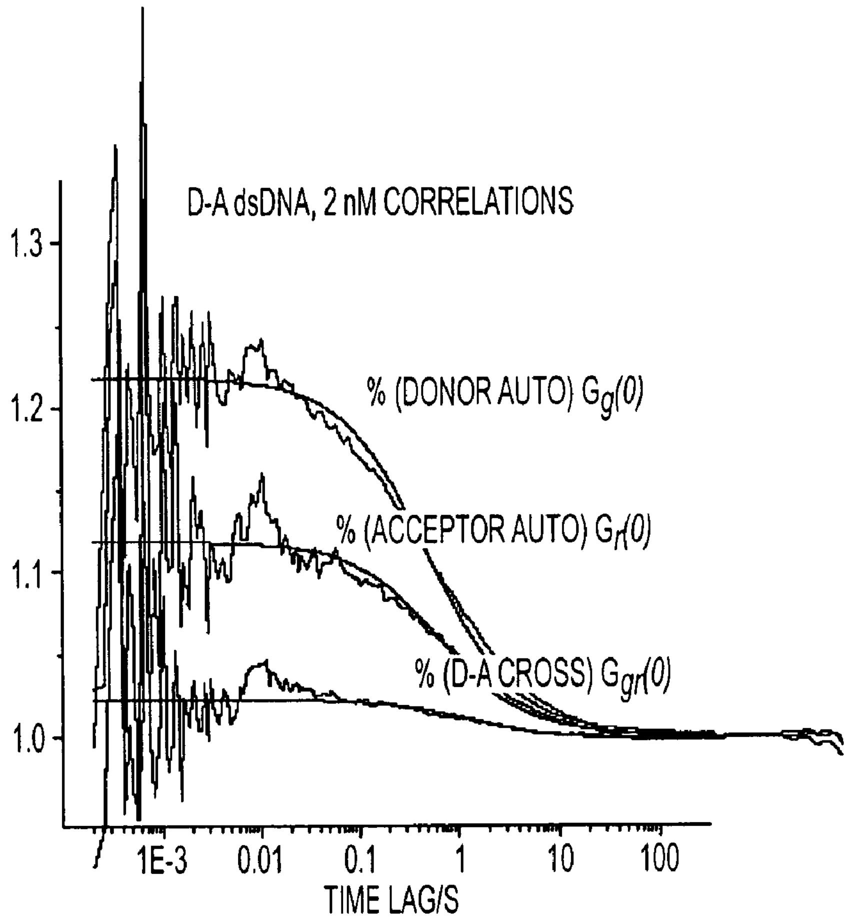
FIG. 15 Top. FCS donor autocorrelation, acceptor autocorrelation, and donor-acceptor cross correlation curves for dsDNA. Bottom. Correlation functions for D and A autocorrelation and D-A cross-correlation. E is the FRET efficiency, and k is the brightness ratio between green and red fluorophores. Concentrations of donor-only ($Y_D$), acceptor-only ($Y_A$) and donor-acceptor pairs ($Y_{DA}$) can be determined using the correlation function.

The second mode of analysis uses fluorescence correlation analysis to determine concentrations and binding rates for higher concentration samples (1 nM to 10 nM). At these concentrations, occupancy of the detection volume increases to approximately five to ten molecules, and single molecules can no longer be detected [54]. To determine subpopulations of free interactants and complexes using FCS, fluorescence intensity is recorded for donor and acceptor excitations over time. The time-dependent fluorescence intensity (F(t)) is then analyzed in terms of its temporal autocorrelation (donor/donor or acceptor/acceptor) and cross-correlation (donor/acceptor). Fittings of these functions provide information on equilibrium concentrations, reaction kinetics and diffusion rates of molecules in the sample. FIG. 15 illustrates this analysis on an interacting system. Auto- and cross-correlation curves are shown on the right, and the correlation functions for each species are presented on the left. By fitting the correlation functions concentrations of the subpopulations, $Y_D$, $Y_A$, and $Y_{DA}$ are extracted, and biomolecular constants are determined (FIG. 15). Effects like cross-talk between the detection channels can significantly effect the determination of concentration in this analysis. By applying ns-ALEX in accordance with the present invention, cross-talk between the donor and acceptor channel is eliminated, significantly increasing the accuracy of the calculations significantly over existing FCS methodologies.

Using our single optical methodology, capable of analyzing a wide dynamic range, quantitative information can be acquired about protein-protein interactions and gene expression levels in a microbe. The ALEX method makes clear advances over current qualitative methods and the complementary data analysis allows for comparison of interaction and expression levels to provide a more complete view of cellular dynamics.

Elucidation Cell Circuitry Nodes in MR-1

Two-Component Signal Transduction in MR-1

Complex biological circuits are composed of a vast array of protein-protein interactions from transient interactions, to induce conformational changes, to the formation of multiprotein complexes [55]. To demonstrate the range of interactions that the methodology of the present invention can detect, we chose an interaction-rich transcriptional regulation scheme that may exert transcriptional control over electron transport and motility protein in MR-1. This scheme of transcription regulation by the molecular machine NtrC [56, 57], as part of the larger two-component signal transduction schemes in MR-1, provides us with a unique model system that has been characterized in other bacteria [56, 58, 59], but continue to have questions relating to the protein-protein interactions involved in transcription activation.

Transcription activation by NtrC occurs through phosphorylation of NtrC (in vivo by NtrB, i vitro by carbamyl phosphate [60]), formation of a homo-oligomer by the NtrC proteins [61-63], and induction of DNA looping intermediate for interaction of NtrC oligomer with the holoenzyme complex of $\sigma^{54}$-RNAP[64, 65, 66]. The protein interactions involved in transcription initiation have been examined with a variety of biochemical techniques, and open question still remain about the formation of the NtrC oligomer, the oligomerization state of NtrC necessary for transcription activation, and the conformation changes induced by the transient interaction between the NtrC oligomer and the holoenzyme complex. These questions can be addressed by examining this circuit with the ALEX methodology in accordance with the present invention to determine protein-DNA and protein-protein interactions and biomolecular constants.

Oligomerization of Enhancer Binding Protein, NtrC

Formation of the NtrC oligomer and the oligomerization state at the promoter can be examined with ALEX. Unphosphorylated NtrC proteins exist as dimers in solution and after phosphorylation, the NtrC proteins organize into a large oligomer. The formation of this large oligomer may occur on the DNA with NtrC dimer binding DNA and through protein-protein interactions directing assembly or oligomer units could form in solution and then assemble on the consensus regions of DNA [67, 68]. ALEX can be used to determine the assembly mechanism of the NtrC oligomer and the stoichiometry of that complex. A universal labeling scheme can be used or single cysteine mutants of NtrC can be created and fluorescently labeled using thiol-reactive fluorescent dyes (Molecular Probes). Oligomerization status and assembly of the NtrC oligomer can be examined using two-color coincident detection and the stoichiometry axis (S) of ALEX. To determine the model of formation, stoichiometry of NtrC can be determined in the absence of DNA and as a control in the presence of fluorescently-labeled DNA lacking a consensus binding site. The stoichiometry of this solution complex can be compared with that determined in the presence of fluorescently-labeled DNA containing NtrC consensus sites.

Activation of transcription by NtrC requires the interactions of the NtrC oligomer with the σ54-RNAP holoenzyme, and this interaction occurs over a large distance. NtrC binding sites can be located over one hundred base pairs (bp) away from the transcription start site [69]. This distance requires the formation of a DNA looped intermediate to activate transcription. Over smaller distances (~100-150 bp), NtrC can induce this looping event [64, 65], but over large distances an additional protein is required for DNA looping. This protein, integration host factor (IHF) induces a 180° u-turn in the DNA to bring the oligomer into contact with the holoenzyme [70].

This additional dimension of complexity in the signaling cascade gives an opportunity to examine transcriptional machinery more completely by extending ALEX analysis to a three-color interaction. The IHF protein is a heterodimer of two small protein subunits, α and β. These subunits interact in solution and bind to specific consensus regions of DNA to induce the u-turn [71]. The ALEX method of the present invention can be used to verify the activity of IHF using a DNA construct with a donor and acceptor molecule conjugated to the 5' and 3' ends, respectively. These labels will undergo FRET when active HF induces the 180° turn [72]. Once activity is verified, cysteine mutants of IHF can be fluorescently labeled and hetero-dimerization of the subunits can be detected by two-color coincidence. Finally, a three-color analysis can be carried out with a donor-labeled NtrC, an acceptor-labeled $\sigma^{54}$, and a fluorphore label on IF, which is spectrally distinct from the donor-acceptor pair and will not undergo resonance energy transfer. This three-color method can be used to probe the complex protein circuit activating transcription over large distances. Coincidence of the proteins on the DNA can be detected and dynamic formation of the DNA looped intermediate can be examined using a D-A pair.

For three-color ALEX in accordance with the present invention, an additional excitation laser may be added to provide modulation between three different wavelength states and data analysis is extended to three-dimensional histograms, where coincidence is measured for each dimension. This methodology can be extended further to n fluorophores resulting in n-dimensional histograms. The only practical limitation being distinct and separable fluorophore excitation and emission.

Another stage of transcription activation that can be explored using ALEX in accordance with the present invention is the interaction of the NtrC oligomer with $\sigma^{54}$ to catalyze the formation of an open transcription complex. NtrC, an ATPase, catalyzes the formation of the open complex through hydrolysis of ATP and an interaction with the σ subunit of the holoenzyme [58, 57]. This interaction has not been well characterized and ALEX can be used to examine association state and conformational dynamics to provide a more complete picture of the dynamics of this very important interaction. Several unique labeling schemes are necessary to examine the interaction of these proteins. Labeling of the protein termini can be accomplished using a site-specific method. Using ALEX's FRET distance determinations, areas of interaction can be identified and $\sigma^{54}$ mutants can be created to modify interaction surfaces to give more in depth understanding of transcription activation.

Cloned MR-1 promoters can be inserted into a plasmid designed for transcriptional analysis of NtrC and $\sigma^{54}$. This plasmid will allow screening of different promoter distances for DNA looping studies, aid in the determination promoter dependency of the NtrC oligomerization state and assay the activity of these recombinant proteins and mutants with fluorescent abortive initiation assay [73].

Mapping of Selected Library of MR-1 Proteins

The scalability of the method of the present invention to high-throughput genome-wide protein-protein interaction mapping can be demonstrated by examining a selected subset of interacting proteins and mapping their pair-wise interactions. With the large number of available MR-1 protein clones from fellow Shewanella Federation members and the national laboratories, there is a large pool from which to select a subset of MR-1 proteins for protein-protein interaction mapping. The interactions mapping can occur in two stages. First, a small library of 6-8 proteins of known function can be screened pair-wise for interacting partners, then a library of up to 20 proteins with known and unknown functions can be examined and interactions mapped to provide functional information about the unknown proteins. For interacting pairs, biomolecular constants, such as $K_d$, $K_a$, and "on and off" rates, can be provided using the present invention.

This small library can serve as a proving-ground for selecting a robust site-specific labeling scheme, and once an optimized labeling scheme is selected the cloned proteins can be inserted into the labeling vector, expressed, purified, and interactions mapped using ALEX.

Quantification of Expression Levels in MR-1

Elucidation of cellular circuits requires both interaction mapping and expression level analysis. Unlike genomes, proteomes are dynamic, and cellular concentrations of proteins are constantly changing due to growth, metabolic activities, and environmental changes [74]. These fluctuations are critical to dynamic cell circuitry, and the changes in expression levels can further characterize protein activities [75]. Therefore, to provide an integrated picture of cellular circuitry and fluxes, the mRNA and protein expression levels of electron transport and regulation proteins, such as two-component signal transduction proteins, can be examined using ALEX in accordance with the present invention to delineate correlation between MRNA and protein expression levels for different growth cycles and environ.

Quantification of mRNA Expression Levels

The transcriptional machinery involved in two-component signal transduction provides an excellent starting point for our mRNA analysis. The alternative sigma factor, $\sigma^{54}$, initiates transcription at specific promoters to provide differential expression for subsets of genes [69]. Regulation of transcription initiation by $\sigma^{54}$ is achieved two ways, first, additional protein component, such as the response regulators, NtrC, are required for transcription initiation, and second, cellular levels of $\sigma^{54}$ are carefully regulated [69]. Therefore, increases in $\sigma^{54}$ mRNA levels indicate necessary expression of its controlled genes. For example, in *E. Coli* nitrogen limiting condition induce expression of $\sigma^{54}$ for the increased transcription of nitrogen fixation genes [56]. By examining expression levels profiles of MR-1 $\sigma^{54}$ for different growth environments, the role of $\sigma^{54}$ in regulation pathways for electron transport proteins can be elucidated.

Development and Validation of mRNA Quantification for $\sigma^{54}$

The ALEX methodology in accordance with the present invention is capable of detecting hybridization events. However, accurate quantification mRNA levels requires standardized signal processing and data analysis. Once these analysis methods are validated, any mRNA target could be quantified using ALEX.

An example of a way to develop quantification analysis, involves using a plasmid containing MR-1 $\sigma^{54}$ in an inducible promoter system, where one can tune the expression of $\sigma^{54}$ in a controlled manner (e.g. an arabinose promoter). Using this controlled promoter system, cell cultures can be grown with different expression levels of $\sigma^{54}$. RNA can be purified from these cultures and detected using two synthetic DNA probes fluorescently-labeled with either a donor or acceptor fluorophore. For concentration determinations, the RNA can be serially diluted to reach pM concentration of the target, and titrated with an increasing concentration of probes. ALEX analysis can be performed on each dilution and the number of coincident donor-acceptor (D-A) events vs. free donor (D) and acceptor (A) can be analyzed. At a very high concentration of primers (compared to the concentration of the mRNA target), free D and A will dominate the 2D ALEX-FAMS histogram; at a very low concentration of primers (compared to the concentration of the mRNA target), D-A complexes will dominate the 2D ALEX-FAMS histogram. The absolute concentration of the target mRNA can be determined by the ALEX analysis of the whole dilution series. ALEX in accordance with the present invention can be used not only to detect rare events in samples containing purified RNA, but can also be used to analyze complex solutions containing mRNA, such as cell lysates [75, 76].

Quantification of $\sigma^{54}$ Protein Expression Levels

The examination of expression levels cannot be limited to mRNA alone. Complex regulation cascades, as well as competing metabolic processes, make protein abundances minimally correlated with mRNA profiles; therefore, examination of cell circuits would be incomplete without protein expression levels.

While the same data analysis techniques can be carried over from mRNA expression quantification, analysis of protein expression levels with ALEX requires two high affinity, mutually exclusive antibodies for any protein of interest. Development of probes for protein quantification is more involved (molecular evolution of scFv) and can take longer time to accomplish. Accordingly, to demonstrate the capabilities of the present method for protein expression level quantification, only a single target for quantification can be used.

Two high affinity, mutually exclusive antibodies against purified wild-type Shewnella $\sigma^{54}$ can be developed by molecular evolution using yeast display. Feldhaus et al. [77] demonstrated evolution of picomolar affinity antibodies after 3 cycles of affinity maturation from the original library of clones. A simple screen of the $\sigma^{54}$ binding clones can elucidate a pair of scFv which bind $\sigma^{54}$ simultaneously. Fluorescent site-specific labeling of the novel $\sigma^{54}$ antibodies can be accomplished by two different approaches. The first uses fluorescently labeled secondary antibodies, specific to an epitope tag, such as example, V5, c-myc, HA, or Flag. These conjugates are readily available through vendors with a variety of fluorescent probes. The second approach utilizes the FlAsH/ReAsH technology previously discussed. These fluorescently labeled antibodies are then used in a solution-based sandwich assay for quantification.

Development and Validation of Protein Quantification for $\sigma^{54}$

An exemplary quantification analysis on the protein level involves the use of the evolved antibodies to quantify purified a Two samples of purified protein are be used for quantification, one from which the antibodies were raised (purified wild-type $\sigma^{54}$) and recombinant $\sigma^{54}$ purified for two-component transduction studies. Purified proteins are serially diluted and titrated with an increasing concentration of antibodies in equimolar ratios. ALEX analysis is performed on each dilution and the number of coincident D-A events vs. free D and A is analyzed for concentration determination. After antibody specificity and affinity has been verified on purified proteins, one can then move the detection of $\sigma^{54}$ to cell lysates.

The present invention may be extended to additional excitation sources and fluorophores (therefore additional emission ranges) and additional ratiometric expressions that increase the ability to resolve species and measure distances within complexes. By combining multiple-excitations with multiple fluorophores (each having a distinct emission), the method can be extended to three or four fluorophores of distinct emissions. This will allow simultaneous FRET-based measurements of multiple distances: three distances for three different fluorophores, and (in principle) six distances using four fluorophores. Multi-color experiments in coordination with the ALEX strategy (to 3-4 colors) will also be able to monitor interactions between 3 or 4 molecules (each labeled with a distinct fluorophore), by checking the coincidence of fluorophores in the resulting multi-component complexes, even if the distance between the fluorophores exceeds the range accessible by FRET. Several ratiometric expressions that emphasize various complexes can be constructed and used to report on the stoichiometry and structure of various complexes present in multi-component mixtures.

Figure 14:
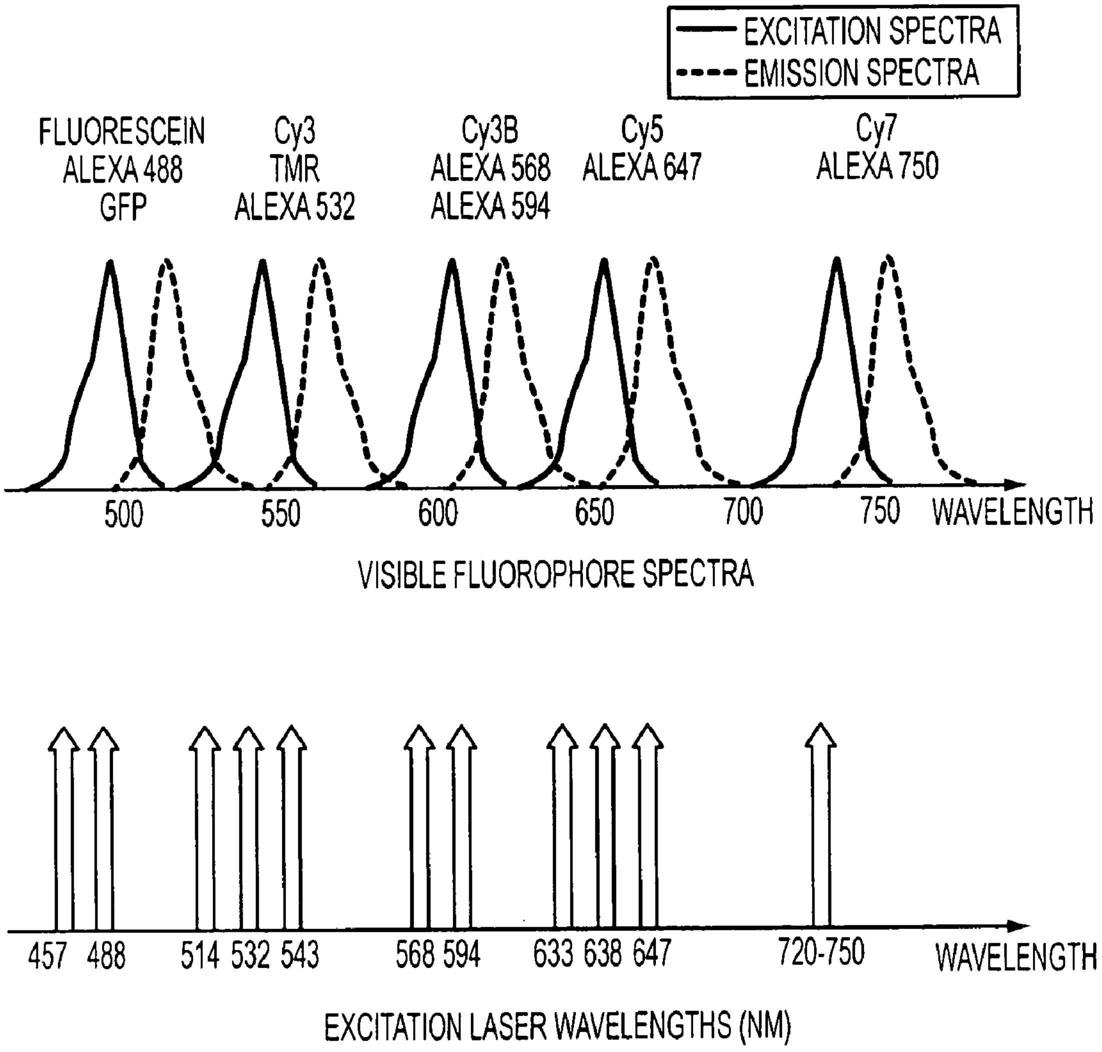
FIG. 14 depicts an exemplary selection of fluorophores that are suitable for use in the method of the present invention, along with corresponding laser sources that are suitable for their excitation.

FIG. 14 is an exemplary selection of fluorophores that can be used in connection with the present invention, grouped by their spectral properties. We have detected smFRET between Alexa488 and TMR, and we routinely perform smFRET between TMR and Cy5. An equivalent combination (fluorescein/TMR/Cy5) has been used previously in ensemble studies (Liu et al. [50]). Moreover, there is a spectral window between TMR and Cy5 (or A647) that can be used to introduce a fourth fluorophore, such as Alexa594, that has already been used as an smFRET acceptor [30], and is a good candidate for 4-color smFRET. The increasing complexity also increases the need for a method that determines the presence or absence of each fluorophore in the molecule under consideration. Thus, one could extend the method to three (or four) fluorophores, by alternating the excitation between two additional lasers. For example, a 594-nm solid-state laser, and a multi-line laser (see FIG. 14). The emitted photons can be split using dichroic mirrors onto 3 or 4 existing APDs. The data acquisition and analysis is then adapted to this multicolor system. In the special case of ET dyes and nanocrystals, a similar ALEX-FRET approach will require only one excitation laser source (no modulation). Similar ratiometric expression and 2D histograms can be developed.

Having thus described exemplary embodiments of the present invention, it should be noted by those skilled in the art that the within disclosures are exemplary only and that various other alternatives, adaptations and modifications may be made within the scope of the present invention. For example, FRET is not required for every embodiment of the present invention. As will be appreciated by one of ordinary skill in the art, the method of the present invention may be used in a wide variety of applications where the fluorophores are sufficiently far apart that FRET does not occur. Accordingly, the present invention is not limited to the above preferred embodiments and examples, but is only limited by the following claims.

REFERENCES

[1] Mendelsohn, A. R. and Brent, R. (1999) Science 284, 1948-50.
[2] Delneri, D., Brancia, F. L. and Oliver, S. G. (2001) Curr Opin Biotechnol 12, 87-91.
[3] Uetz, P. et al. (2000) Nature 403, 623-7
[4] Uetz, P. (2002) Curr Opin Chem Biol 6, 57-62.
[5] Hazbun, T. R. and Fields, S. (2001) Proc Natl Acad Sci USA 98, 4277-8.
[6] Ito, T., Chiba, T., Ozawa, R., Yoshida, M., Hattori, M. and Sakaki, Y. (2001) Proc Natl Acad Sci USA 98, 4569-74.
[7] Oliver, S. (2000) Nature 403, 601-3.
[8] Legrain, P. and Selig, L. (2000) FEBS Lett 480, 32-6.
[9] Magde, D., Elson, E. and Webb, W. W. (1972) Physical Review Letters 29, 705-8.
[10] Schwille, P., Oehlenschlager, F. and Walter, N. G. (1996) Biochemistry 35, 10182-93.
[11] Kinjo, M. and Rigler, R. (1995) Nucleic Acids Res 23, 1795-9.
[12] Rauer, B., Neumann, E., Widengren, J. and Rigler, R. (1996) Biophys Chem 58, 3-12.
[13] Qian, H. and Elson, E. L. (1990) Biophysical Journal 57, 375-80.
[14] Kask, P., Palo, K., Ullmann, D. and Gall, K. (1999) Proc Natl Acad Sci USA 96, 13756-61.
[1c5] Chen, Y., Müller, J. D., So, P. T. and Gratton, E. (1999) Biophysical Journal 77, 553-67.
[16] Chen, Y., Muller, J. D., Tetin, S. Y., Tyner, J. D. and Gratton, E. (2000) Biophysical Journal 79, 1074-1084.
[17] Palo, K., Mets, U., Jäger, S., Kask, P. and Gall, K. (2000) Biophysical Journal 79, 2858-66.
[18] Schwille, P., Meyer-Almes, F. J. and Rigler, R. (1997) Biophysical Journal 72, 1878-86.
[19] Heinze, K. G., Koltermann, A. and Schwille, P. (2000) Proceedings of the National Academy of Sciences of the United States of America 97, 10377-82.
[20] Lee, L. G. et al. (1997) Nucleic Acids Res 25, 2816-22.
[21] Bruchez, M., Jr., Moronne, M., Gin, P., Weiss, S. and Alivisatos, A. P. (1998) Science 281, 2013-6.
[22] Lacoste, T. D., Michalet, X., Pinaud, F., Chemla, D. S., Alivisatos, A. P. and Weiss, S. (2000) Proc Natl Acad Sci USA 97, 9461-6.
[23] Kask, P. et al. (2000) Biophys J 78, 1703-13.
[24] Dahan, M., Deniz, A. A., Ha, T., Chemla, D. S., Schultz, P. G. and Weiss, S. (1999) Chemical Physics 247, 85-106.
[25] Deniz, A. A., Dahan, M., Grunwell, J. R., Ha, T., Faulhaber, A. E., Chemla, D. S., Weiss, S. and Schultz, P. G. (1999) Proceedings of the National Academy of Sciences of the United States of America 96, 3670-5.
[26] Deniz, A. A. et al. (2000) Proc Natl Acad Sci USA 97, 5179-84.
[27] Clegg, R. M. (1992) Methods Enzymol 211, 353-88.
[28] Selvin, P. R. (2000) Nat Struct Biol 7, 730-4.
[29] Ha, T., Enderle, T., Ogletree, D. F., Chemla, D. S., Selvin, P. R. and Weiss, S. (1996) Proc Natl Acad Sci USA 93, 6264-8.
[30] Schuler, B., Lipman, E. A. and Eaton, W. A. (2002) Nature 419, 743-7.
[31] Zhuang, X., Bartley, L. E., Babcock, H. P., Russell, R., Ha, T., Herschlag, D. and Chu, S. (2000) Science 288, 2048-51.
[32] Zhuang, X., Kim, H., Pereira, M. J., Babcock, H. P., Walter, N. G. and Chu, S. (2002) Science 296, 1473-6.
[33] Rothwell, P. J. et al. (2003) Proc Natl Acad Sci USA 100, 1655-60.
[34]Ha, T., Rasnik, I., Cheng, W., Babcock, H. P., Gauss, G. H., Lohman, T. M. and Chu, S. (2002) Nature 419, 638-41.
[35] Kohl, T., Heinze, K. G., Kuhlemann, R., Koltermann, A. and Schwille, P. (2002) Proc Natl Acad Sci USA 99, 12161-6.
[36] Eggeling, C., Fries, J. R., Brand, L., Günther, R. and Seidel, C. A. (1998) Proceedings of the National Academy of Sciences of the United States of America 95, 1556-61.
[37] Fries, J. R., Brand, L., Eggeling, C., Kollner, M. and Seidel, C. A. M. (1998) Journal of Physical Chemistry a 102, 6601-6613.
[38] Eggeling, C., Widengren, J., Rigler, R. and Seidel, C. A. M. (199S) Anal chem 70, 2651-2659.
[39] Kapanidis, A., Lee, N. K., Laurence, T., Margeat, E., Doose, S. and Weiss, S. (2003) Proc. Nat. Acad. Sci. USA, in preparation.
[40] Ha, T., Ting, A. Y., Liang, J., Caldwell, W. B., Deniz, A.A., Chemla, D. S., Schultz, P. G. and Weiss, S. (1999) Proc Natl Acad Sci USA 96, 893-8.
[41] Pandolfi, P. P. (2001) Oncogene 20, 3116-27.
[42] Holden, J. A. (2001) Curr Med Chem Anti-Canc Agents 1, 1-25.
[43] Heyduk, E., Knoll, E. and Heyduk, T. (2003) Anal Biochem 316, 1-10.
[44] Heyduk, T. and Heyduk, E. (2002) Nat Biotechnol 20, 171-6.
[45] Heyduk, E., Fei, Y. and Heyduk, T. (2003) Comb Chem High Throughput Screen 6, 347-54.
[46] Ko, D. S., Sauer, M., Nord, S., Müller, R. and Wolfrum, J. (1997) Chemical Physics 269, 54-58.
[47] Kapanidis, A. N., Ebright, Y. W. and Ebright, R. H. (2001) J Am Chem Soc 123, 12123-5.
[48] Laurence, T. A. and Weiss, S. (2003) Science 299, 667-8.
[49] Levene, M. J., Korlach, J., Turner, S. W., Foquet, M., Craighead, H. G. and Webb, W. W. (2003) Science 299, 682-6.
[50] Liu, J. and Lu, Y. (2002) J. Am. Chem. Soc. 124, 15208-16.
[51] Kapanidis, A. N., and S. Weiss, *Fluorescent probes and bioconjugation chemistries for single-molecule fluorescence analysis of biomolecules*. Journal of Chemical Physics, 2002. 117(24): p. 10953-10964.
[52] Adams, S. R., et al., *New Biarsenical Ligands and Tetracysteine Motifs for Protein Labeling in Vitro and in Vivo:*

*Synthiesis and Biological Applications. J. Am. Chem. Soc.*, 2002. 124(21): p. 6063-6076.

[53] Schuler, B. and L. K. Pannell, *Specific Labeling of Polypeptides at Amino-Terminal Cysteine Residues Using Cy5-benzyl Thioester*. Bioconjugate Chem., 2002. 13(5): p. 1039 -1043.

[54] Laurence, T. A. and S. Weiss, *ANALYTICAL CHEMISTRY: How to Detect Weak Pairs*. Science, 2003. 299(5607): p. 667-668.

[55] Nooren, I. M. A. and J. M. Thornton, *NEW EMBO MEMBER'S REVIEW: Diversity of protein-protein interactions*. EMBO J., 2003. 22(14): p. 3486-3492.

[56] Hoch, J. A. and T. J. Silhavy, eds. *Two-Component Signal Transduction*. 1995, ASM Press: Washington, D.C.

[57] Rombel, I., et al., *MgATP Binding and Hydrolysis Determinants of NtrC, a Bacterial Enhancer-Binding Protein*. J. Bacteriol., 1999. 181(15): p. 4628-4638.

[58] Lee, J., et al., *Phosphorylation-Induced Signal Propagation in the Response Regulator NtrC. J. Bacteriol.*, 2000. 182(18): p. 5188-5195.

[59] Tintut, Y., J. T. Wang, and J. D. Gralla, *Abortive Cycling and the Release of Polymerase for Elongation at the * 54-*dependent glnAp*2 *Promoter*. J. Biol. Chem., 1995. 270(41): p. 24392-24398.

[60] Wang, J. T. and J. D. Gralla, *The Transcription Initiation Pathway of Sigma* 54*Mutants That Bypass the Enhancer Protein Requirement. IMPLICATIONS FOR THE MECHANISM OF ACTIVATION*. J. Biol. Chem., 1996. 271(51): p. 32707-32713.

[61] Wyman, C., et al., *Unusual Oligomerization Required for Activity of NtrC, a Bacterial Enhancer-Binding Protein*. Science, 1997. 275(5306): p. 1658-1661.

[62] Sevenich, F., et al., *DNA binding and oligomerization of NtrC studied by fluorescence anisotropy and fluorescence correlation spectroscopy*. Nucl. Acids. Res., 1998. 26(6): p. 1373-1381.

[63] Rippe, K., N. Mucke, and A. Schulz, *Association States of the Transcription Activator Protein NtrC from E. coli Determined by Analytical Ultracentrifugation*. Journal of Molecular Biology, 1998. 278(5): p. 915-933.

[64] Rippe, K., et al., *Transcriptional Activation via DNA-looping: Visualization of Intermediates in the Activation Pathway of E. coli RNA Polymerase. [sigma]* 54*Holoenzyme by Scanning Force Microscopy*. Journal of Molecular Biology, 1997. 270(2): p. 125-138.

[65] Su, W., et al., *DNA-Looping and Enhancer Activity: Association Between DNA-Bound NtrC Activator and RNA Polymerase at the Bacterial glnA Promoter*. PNAS, 1990. 87(14): p. 5504-5508.

[66] Schulz, A., et al., *Scanning Force Microscopy of Escherichia coli RNA Polymerase. [sigma]* 54*Holoenzyme Complexes with DNA in Buffer and in Air*,. Journal of Molecular Biology, 1998. 283(4): p. 821-836.

[67] Porter S C, N. A., Wedel A B, Kustu S., *Oligomerzizationi of NTRC at the glnA enhancer is required for transcriptional activation*. Genes Dev., 1993. 7(11): p. 2258-73.

[68] Rippe, K., *Simultaneous Binding of Two DNA Duplexes to the NtrC-Enhancer Complex Studied by Two-Color Cross-Correlation Spectroscopy*. Biochemistry, 2000. 39(9): p. 2131-2139.

[69] Wagner, R., *Transcription Regulation in Prokaryotes*. 2000, Oxford: Oxford University Press.

[70] Santero E, H. T., North A K, Berger D K, Porter S C, Kustu S., *Role of integration host factor in stimulating transcription from the sigma* 54-*dependent nifH promoter*. J Mol Biol., 1992. 227(3): p. 602-20.

[71] Bewley, C. A., A. M. Gronenborn, and G. M. Clore, *MINOR GROOVE-BINDING ARCHITECTURAL PROTEINS. Structure, Function, and DNA Recognition*. Annual Review of Biophysics and Biomolecular Structure, 1998. 27(1): p. 105-131.

[72] Lorenz, M., et al., *Global structure similarities of intact and nicked DNA complexed with IHF measured in solution by fluorescence resonance energy transfer*. Nucl. Acids. Res., 1999. 27(23): p. 4619-4625.

[73] Kolasa I K, L. T., Wierzchowski K L., *Effect of A(n) tracts within the UP element proximal subsite of a model promoter on kinetics of opens complex formation by Escherichia coli RNA polymerase*. Acta Biochim Pol., 2002. 49(3): p. 659-69.

[74] Kettman J R, F. J., Lefkovits I., *Proteome, transcriptome and genome: top down or bottom up analysis?*Biomol Eng., 2001. 18(5): p. 207-12.

[75] Giometti C S, K. T., Tollaksen S L, Tsapin A, Zhu W, Yates JR 3rd, Nealson K H., *Analysis of the Shewanella oneidensis proteome by two-dimensional gel electrophoresis under nondenaturing conditions*. Proteomics, 2003. 3(5): p. 777-85.

[76] Beliaev, A. S., et al., *Gene and Protein Expression Profiles of Shewanella oneidensis during Anaerobic Growth with Different Electron Acceptors*. OMICS, 2002. 6(1): p. 39-60.

[77] Feldhaus, M., et al., *Flow-cytometric isolation of human antibodies from a nonimmune Saccharomyces cerevisiae surface display library*. Nat Biotechnol., 2003. 21(2): p.163-70.

What is claimed is:

1. A method for analyzing a sample to determine information about one or more molecules that may be present in said sample, said method comprising the steps of:

providing a sample in a detection zone wherein said sample comprises at least one molecule that is labeled with at least one fluorophore to provide a labeled molecule wherein said fluorophore remains within said detection zone for a detection period, said fluorophore being capable of emitting a signal wherein said signal has properties comprising wavelength, intensity, lifetime, and polarization;

exposing said labeled molecule to radiation within said detection zone wherein said radiation has properties comprising wavelength, intensity, lifetime and polarization;

modulating at least one of the properties of said radiation by changing said at least one property from an initial state to at least one subsequent state and then changing said at least one property back from said at least one subsequent state to said initial state wherein said modulating of said one or more properties occurs over a modulation period and wherein said modulation period is equal to or less than said detection period;

measuring at least one of said properties of said signal emitted by said fluorophore while said fluorophore is located within said detection zone to obtain an emission profile; and using said emission profile to determine information about said one or more molecules that may be present in said sample.

2. A method for analyzing a sample according to claim 1 wherein the size of said detection zone is from 50 nm to 20 μm.

3. A method for analyzing a sample according to claim 1 wherein said modulation period is at least ten times smaller than said detection period.

4. A method for analyzing a sample according to claim 1 wherein said modulation period is less than 1 millisecond.

5. A method for analyzing a sample according to claim 1 wherein said sample comprises at least one molecule that is not labeled with a fluorophore and wherein said emission profile is used to determine information about said molecule that is not labeled with a fluorophore.

6. A method for analyzing a sample according to claim 1 wherein said labeled molecule comprises at least two different fluorophores.

7. A method for analyzing a sample according to claim 1 wherein said sample comprises at least two different labeled molecules.

8. A method for analyzing a sample according to claim 7 wherein said sample comprises at least three different labeled molecules.

9. A method for analyzing a sample according to claim 8 wherein said sample comprises at least four different labeled molecules.

10. A method for analyzing a sample according to claim 6 wherein said labeled molecule comprises at least three different fluorophores.

11. A method for analyzing a sample according to claim 10 wherein said labeled molecule comprises at least four different fluorophores.

12. A method for analyzing a sample according to claim 1 wherein said at least one labeled molecule comprises one or more molecule selected from the group consisting of nucleic acids, proteins, nucleotides, peptides, fluorophore-chelator conjugates, peptide nucleic acids, lipids, sugars, and hybrids thereof.

13. A method for analyzing a sample according to claim 5 wherein said at least one molecule that is not labeled comprises one or more molecules selected from the group consisting of nucleic acids, proteins, nucleotides, peptides, peptide nucleic acids, lipids, sugars, and hybrids thereof.

14. A method for analyzing a sample according to claim 6 wherein said labeled molecule comprises a molecule selected from the group consisting of nucleic acids, proteins, nucleotides, peptides, fluorophore-chelator conjugates, peptide nucleic acids, lipids, sugars, and hybrids thereof.

15. A method for analyzing a sample according to claim 1 wherein said step of using said emission profile to determine information about said one or more molecules that may be present in said sample comprises calculating ratiometric expressions from said signals emitted by the said fluorophore and forming one or more histograms.

16. A method for analyzing a sample according to claim 1 wherein the number of molecules present in said detection zone at any one time is less than 10.

17. A method for analyzing a sample according to claim 5 wherein said emission profile is used to determine information comprising information about any interaction between said labeled molecule and said molecule that is not labeled.

18. A method for analyzing a sample according to claim 6 wherein said emission profile is used to determine information about the structure of said labeled molecule.

19. A method for analyzing a sample according to claim 1 wherein the property of said radiation that is modulated comprises said wavelength.

20. A method for analyzing a sample according to claim 1 wherein said modulating step comprises changing said at least one property from said initial state to at least two subsequent states before changing said at least one property back to said initial state.

21. A method for analyzing a sample to determine information about one or more molecules that may be present in said sample, said method comprising the steps of:

providing a sample in a detection zone wherein said sample comprises at least one molecule that is labeled with at least one fluorophore to provide a labeled molecule, said fluorophore being capable of emitting a signal wherein said signal has properties comprising wavelength, intensity, lifetime and polarization and wherein said one or more molecules undergo a change in state between a first molecular state and a second molecular state during a period of time while said molecule(s) are in said detection zone;

exposing said labeled molecule to radiation within said detection zone wherein said radiation has properties comprising wavelength, intensity, lifetime and polarization;

modulating at least one of the properties of said radiation by changing said at least one property from an initial state to at least one subsequent state and then changing said at least one property back from said at least one subsequent state to said initial state wherein said modulating of said one or more properties occurs over a modulation period and wherein said modulation period is equal to or less than the period of time during which said molecule changes from said first molecular state to said second molecular state;

measuring at least one of said properties of said signal emitted by said fluorophore while said fluorophore is located within said detection zone to obtain an emission profile; and using said emission profile to determine information about said change in state of said one or more molecules that may be present in said sample.

22. A method for analyzing a sample according to claim 21 wherein said period of time during which said change in state takes place is at least ten times greater than said modulation period.

23. A method for analyzing a sample according to claim 22 wherein said modulation period is less than 250 microseconds.

24. A method for analyzing a sample according to claim 21 wherein said sample comprises at least one molecule that is not labeled with a fluorophore and wherein said emission profile is used to determine information about said molecule that is not labeled with a fluorophore.

25. A method for analyzing a sample according to claim 21 wherein said labeled molecule comprises at least two different fluorophores.

26. A method for analyzing a sample according to claim 21 wherein said sample comprises at least two different labeled molecules.

27. A method for analyzing a sample according to claim 26 wherein said sample comprises at least three different labeled molecules.

28. A method for analyzing a sample according to claim 27 wherein said sample comprises at least four different labeled molecules.

29. A method for analyzing a sample according to claim 25 wherein said labeled molecule comprises at least three different fluorophores.

30. A method for analyzing a sample according to claim 29 wherein said labeled molecule comprises at least four different fluorophores.

31. A method for analyzing a sample according to claim 21 wherein said at least one labeled molecule comprises one or more molecule selected from the group consisting of nucleic acids, proteins, nucleotides, peptides, fluorophore-chelator conjugates, peptide nucleic acids, lipids, sugars, and hybrids thereofs.

32. A method for analyzing a sample according to claim 24 wherein said at least one molecule that is not labeled comprises one or more molecules selected from the group consisting of nucleic acids, proteins, nucleotides, peptides, peptide nucleic acids, lipids, sugars, and hybrids thereof.

33. A method for analyzing a sample according to claim 25 wherein said labeled molecule comprises a molecule selected from the group consisting of nucleic acids, proteins, nucleotides, peptides, fluorophore-chelator conjugates, peptide nucleic acids, lipids, sugars, and hybrids thereof.

34. A method for analyzing a sample according to claim 21 wherein said step of using said emission profile to determine information about said change in state of said one or more molecules that may be present in said sample comprises calculating ratiometric expressions from said signals emitted by the said fluorophore and forming one or more histograms.

35. A method for analyzing a sample according to claim 21 wherein the number of individual molecules present in said detection zone at any one time is greater than ten.

36. A method for analyzing a sample according to claim 24 wherein said emission profile is used to determine information comprising information about any interaction between said labeled molecule and said molecule that is not labeled.

37. A method for analyzing a sample according to claim 25 wherein said emission profile is used to determine information about the structure of said labeled molecule.

38. A method for analyzing a sample according to claim 21 wherein the property of said radiation that is modulated comprises said wavelength.

* * * * *